US010408813B2

(12) United States Patent
King et al.

(10) Patent No.: US 10,408,813 B2
(45) Date of Patent: Sep. 10, 2019

(54) BIOSENSOR FOR DETECTING INTRACELLULAR CYCLIC ADENOSINE MONOPHOSPHATE (CAMP) AND USES THEREOF

(71) Applicant: Academia Sinica, Taipei (TW)

(72) Inventors: Klim King, Taipei (TW); Yu-Heng Cheng, Taipei (TW)

(73) Assignee: Academia Sinica, Taipei (TW)

( * ) Notice: Subject to any disclaimer, the term of this patent is extended or adjusted under 35 U.S.C. 154(b) by 288 days.

(21) Appl. No.: 15/136,016

(22) Filed: Apr. 22, 2016

(65) Prior Publication Data

US 2016/0313251 A1   Oct. 27, 2016

Related U.S. Application Data

(60) Provisional application No. 62/151,043, filed on Apr. 22, 2015.

(51) Int. Cl.
*G01N 1/00* (2006.01)
*G01N 33/483* (2006.01)
*A61K 31/164* (2006.01)
*A61K 31/231* (2006.01)

(52) U.S. Cl.
CPC ....... *G01N 33/4833* (2013.01); *A61K 31/164* (2013.01); *A61K 31/231* (2013.01); *G01N 2500/10* (2013.01)

(58) Field of Classification Search
CPC .................................................. G01N 2500/10
See application file for complete search history.

(56) References Cited

U.S. PATENT DOCUMENTS

2014/0350100 A1   11/2014   King et al.
2015/0005237 A1   1/2015    Stefan et al.

FOREIGN PATENT DOCUMENTS

WO      2006/054167 A2      5/2006
WO   WO 2006/099160 A1 *   9/2006   ............... C12Q 1/66
WO   WO 2007/039305 A1 *   4/2007   ............. C07K 14/47

OTHER PUBLICATIONS

Brown et al. (2014, JBC, vol. 289(12), pp. 8217-8230) (Year: 2014).*
Wang et al. (2002, Mol. Genet. Genomics, vol. 268, pp. 160-168) (Year: 2002).*
Schmidt et al. (2013, Pharmcol. Rev., vol. 65, pp. 670-709) (Year: 2013).*

* cited by examiner

*Primary Examiner* — Thaian N Ton
*Assistant Examiner* — David A. Montanari
(74) *Attorney, Agent, or Firm* — Juan Carlos A. Marquez; Marquez IP Law Office, PLLC

(57) ABSTRACT

Cyclic adenosine monophosphate (cAMP) biosensors comprising a *Renilla* luciferase (RLuc), a green fluorescent protein (GFP), and an exchange protein activated by cAMP, and uses thereof in determining cAMP levels both in vivo and in vitro. Another aspect of the invention relates to methods for controlling blood glucose levels.

12 Claims, 9 Drawing Sheets
Specification includes a Sequence Listing.

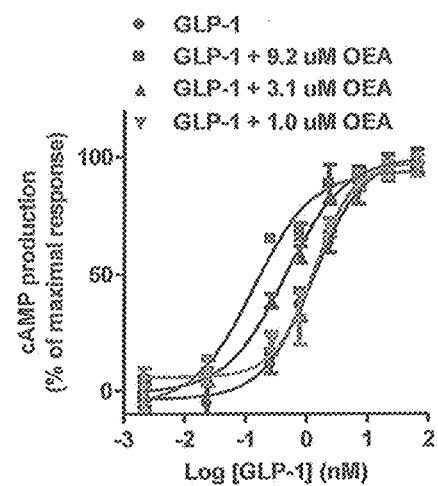
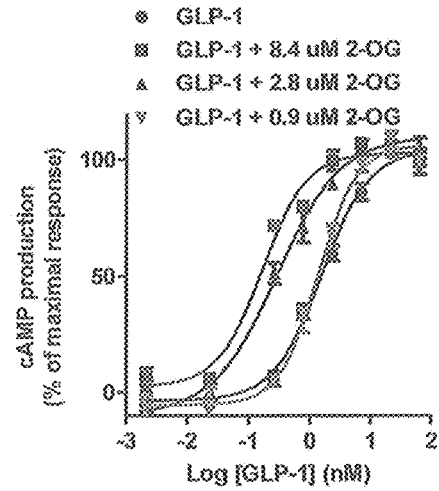
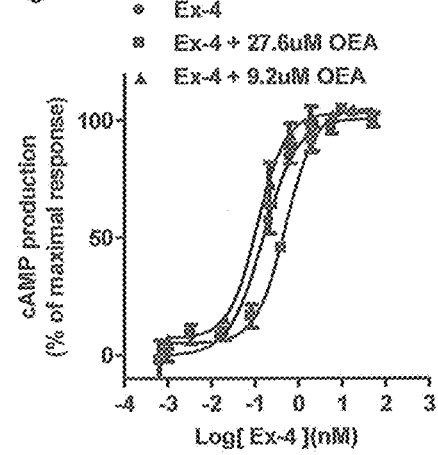
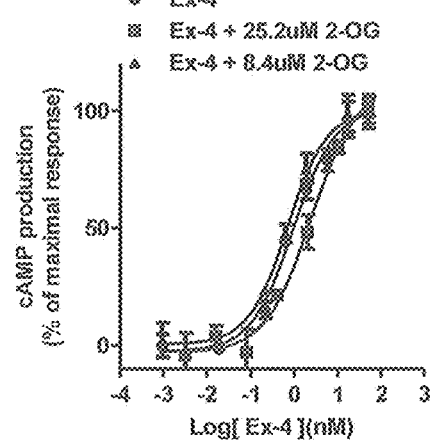
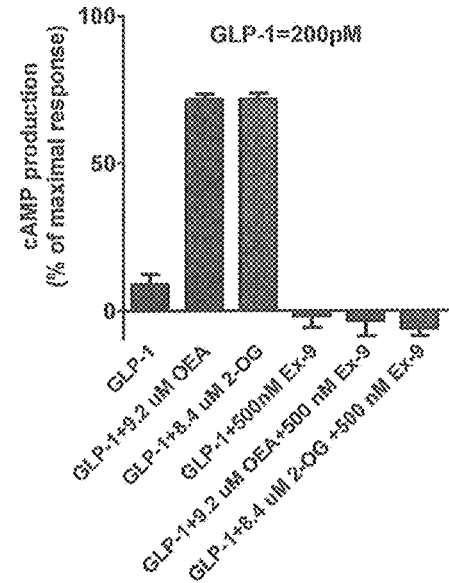

Figure 6A
HAEGTFTSDVSSYLEGQAAKEFIAWLVKGR-6(His)
(SEQ ID NO: 6)
Figure 6B
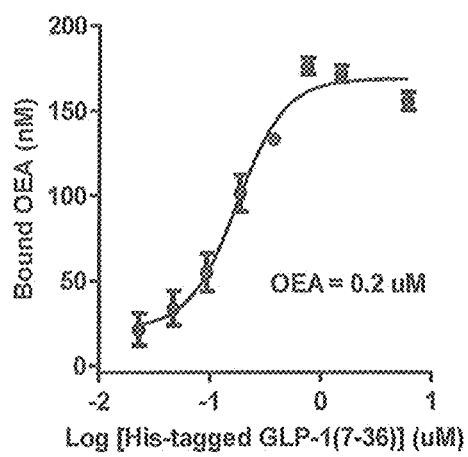
Figure 6C
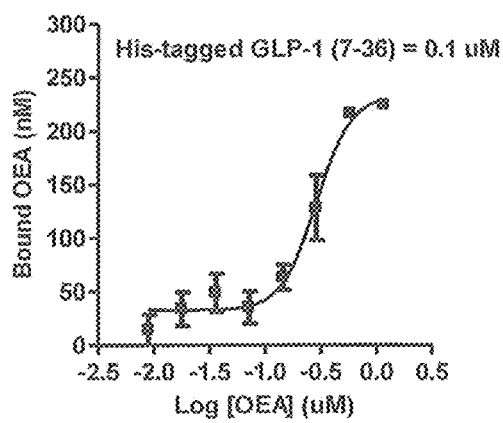
Figure 6D
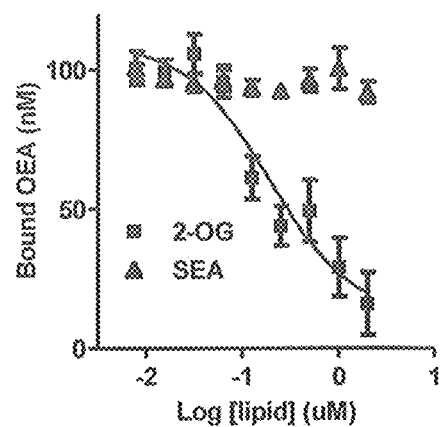

BIOSENSOR FOR DETECTING INTRACELLULAR CYCLIC ADENOSINE MONOPHOSPHATE (CAMP) AND USES THEREOF

RELATED APPLICATION

The present application claims priority under 35 U.S.C. § 119(e) to U.S. Provisional Patent Application No. 62/151,043, filed Apr. 22, 2015, the content of which is herein incorporated by reference in its entirety.

TECHNOLOGY FIELD

The present invention relates to a cAMP detection technology. In particular, the present invention relates to a biosensor for detecting intracellular cAMP and uses thereof.

BACKGROUND OF THE INVENTION

Cyclic adenosine monophosphate (cAMP, also known as cyclic AMP or 3'-5'cyclic adenosine monophosphate) is a second messenger involved in many biological processes in many organisms. For example, cAMP plays important roles in intracellular signal transduction in many organisms. The cAMP-dependent signal transduction pathway is a G protein-coupled receptor (GPGR)-triggered signaling cascade, which mediates various biological processes, e.g., glycogen, sugar, and lipid metabolism.

The bioluminescence resonance energy transfer (BRET) methods are based on resonance energy transfer between a light-emitting enzyme and a fluorescent acceptor. Bacart et al., Biotechnol. J. 3:311-324 (2008); Barak et al., Mol. Pharma. 74:585-594 (2008). Because the BRET technology is cell-based and non-destructive, it is well suited for proteomics applications, including studies on protein-protein interactions. However, to reduce cAMP detection background and obtain better separation of the donor and acceptor energy emission peaks, improvements in BRET assays are needed.

Glucagon-like peptide-1 receptor (GLP-1R) signaling is an established therapeutic target for type 2 diabetes. In addition to human pancreatic islet β cells, GLP-1R is expressed in a wide array of tissues, including lung, heart, kidney, blood vessels, neurons, and lymphocytes (1-4). Mice deficient in GLP-1R expression or with blunted GLP-1R function show impairment of physiologic features not limited to glucose homeostasis but also include learning and memory (4). Clinical trials targeting GLP-1 signaling to treat non-metabolic diseases include those for psoriasis, heart disease, and neurodegenerative diseases (5-7). Despite encouraging outcomes with GLP-1 analogs in reducing myocardial infarct size in acute coronary occlusion (7) and improving clinical symptoms in patients with Parkinson's disease (5), the mechanisms of physiological regulation of GLP-1R signaling beyond energy homeostasis remain largely unknown.

GLP-1 is an incretin peptide hormone derived from post-translational processing of the precursor proglucagon in intestinal L cells (8). On food intake, the biologically active forms of GLP-1 (7-36) amide and GLP-1 (7-37) are secreted, thus increasing the basal plasma level by 3- to 4-fold, to maintain normoglycemia by enhancing glucose-dependent insulin secretion and suppressing glucagon function (8,9). Circulating GLP-1 has a short plasma half-life of only a few minutes due to renal clearance after rapid enzymatic inactivation by a plasma enzyme, dipeptidyl peptidase 4 (DPP 4) (10). Other cells outside of the gut shown to produce GLP-1 include pancreatic α cells and neurons in the localized area of the brain stem (4,11-14), but our knowledge of the physiological regulation of GLP-1 secretion by these cells is limited.

In the brain, GLP-1 is synthesized primarily by a discrete group of neurons located in the nucleus of the solitary tract (12). These neurons send abundant projections to other regions of the brain, including forebrain, hypothalamus, amygdala, stria terminalis, and thalamus, where GLP-1Rs are expressed; this neuronal circuit of GLP-1 signaling is considered relevant to satiety and energy homeostasis (2,11). GLP-1R is also expressed in neurons in the hippocampus (1) and dopaminergic neurons in substantia nigra (3)—where no known GLP-1-secreting neuron innervation is found (3,14). It has been suggested that the basal circulating GLP-1 level is the primary source of ligands accessible to GLP-1Rs in these brain regions and probably in the heart as well. Therefore, determining the mechanism by which basal level of GLP-1 can activate receptors in these brain regions is germane.

The well-delineated functions of GLP-1 are mainly mediated by activation of GLP-1R (4). GLP-1R, as a member of the class B G protein-coupled receptor (GPCR) family, is the only known receptor with high specific affinity for GLP-1. GLP-1R activation leads to two major signaling pathways, namely Gαs coupling and recruitment of β-arrestin to the agonist-occupied receptor; the former mainly leads to activation of adenylyl cyclase, with subsequent generation of cAMP (15), and the latter leads to receptor endocytosis and activation of extracellular signal regulated kinase (ERK) 1/2 signaling (4). In pancreatic β cells, the increased cAMP level is responsible for glucose-dependent insulin release (16) and contributes to maintaining glucose homeostasis. Thus, cAMP production is measured and used as GLP-1R-mediated functional response in properly designed assays.

GLP-1 receptor (GLP-1R) is expressed in many peripheral and neuronal tissues, and is activated by circulating GLP-1. Other than food intake, little is known about factors regulating GLP-1 secretion. Analysis of food intake-induced increase in GLP-1 level and subsequent activation of GLP-1R have provided some insights into the role of GLP-1R signaling in energy homeostasis. However, the short half-life and low basal level of circulating GLP-1 (7-36) amide do not permit assessment of the physiological relevance of GLP-1R signaling other than energy homeostasis.

Current GLP-1 analogue therapeutics requires frequent subcutaneous administrations, and leads to reduced compliance and high prices in developing area. Typically, the plasma level of active GLP-1 is around 5 to 10 μM in the basal state, quickly rises to 20 to 50 μM after oral glucose or meal and will slowly declines to basal level over 2 hours. However, GLP-1 analogue therapeutics usually require to maintain constantly a supra-physiological level of GLP-1 analogues, thus lead to activating GLP-1 receptors constitutively and may cause severe complications upon chronic treatment. Identification of novel compounds that modulate the endogenous GLP-1 receptor signaling pathways can lead to the development of new therapeutics useful in regulating blood glucose levels, thereby treating diabetes or disorders associated with the GLP-1 receptor.

SUMMARY OF THE INVENTION

The present disclosure is based on the discovery that a modified construction of a cAMP biosensor offers the improved real-time detection of intracellular cAMP levels, and the uses thereof can successfully identify agents that exhibit promising effects in inducing cAMP production in vitro and/or in vivo. The present disclosure is also based on a surprising discovery that the binding of some specific endocannabinoid-like lipids, such as oleoylethanolamide (OEA) and 2-oleoylglycerol (2-OG), to GLP-1 enhances the activation of GLP-1R signaling pathway, thereby stimulating cAMP production. This finding implies that the endocannabinoid-like compounds act as agonists in presence of GLP-1 for activation of GLP-1R signaling, and are useful for GLP-1-based therapies.

Accordingly, one aspect of the present disclosure features the design of a biosensor useful for detecting cAMP. The biosensor comprises a protein complex that includes an exchange protein activated by cAMP (Epac) polypeptide, a *Renilla* luciferase (RLuc, such as RLuc8), and a green fluorescent protein (GFP such as GFP2). A cell expressing the biosensor is also provided in the present invention. The Epac polypeptide can be a truncated mutant, which lacks the N-terminal fragment corresponding to residues 1-147 of SEQ ID NO:1. Alternatively, the Epac polypeptide contains point mutations T781A and F782A as compared to a wild-type counterpart. In one example, the Epac polypeptide comprises the amino acid sequence of SEQ ID NO:2.

In some embodiments, the cAMP biosensor comprises a fusion protein, in which the N-terminus and C-terminus of the Epac polypeptide are fused to the RLuc and GFP. In some examples, the RLuc is fused to the N-terminus of the Epac polypeptide via a protein linker (e.g., peptide LGL). Alternatively or in addition, the GFP is fused to the C-terminus of the Epac polypeptide via a protein linker (e.g., peptide AT). In one specific example, the fusion protein comprises the amino acid sequence of SEQ ID NO:3.

In another aspect, the present disclosure features a method for detecting cAMP in a sample, comprising: (i) contacting a cAMP biosensor with a sample in the presence of a luciferase substrate, wherein the biosensor comprises a protein complex that comprises an Epac polypeptide, a RLuc (e.g., RLuc8), and a GFP (e.g., GFP2); (ii) measuring a first luminescent signal at a wave length of around 370-450 nm and a second luminescent signal at a wave length of 500-530 nm; and (iii) determining the presence or level of cAMP in the sample based on a ratio between the first luminescent signal and the second luminescent signal. The cAMP biosensor can be a fusion protein, in which the N-terminus and C-terminus of the Epac polypeptide are fused to the RLuc and GFP. For example, the fusion protein can comprise the amino acid sequence of SEQ ID NO:3.

In one example, the Epac polypeptide is a truncated mutant, which lacks the N-terminal fragment corresponding to residues 1-147 of SEQ ID NO:1. Alternatively or in addition, the Epac polypeptide contains point mutations T781A and F782A as compared to a wild-type counterpart. In one example, the Epac polypeptide comprises the amino acid sequence of SEQ ID NO:2.

In yet another aspect, the present disclosure features an assay system for determining intracellular cAMP levels, comprising a cultured cell that expresses a cAMP sensor, which is a protein complex comprising an Epac polypeptide, a RLuc (e.g., RLuc8), and a GFP (e.g., GFP2). The cAMP biosensor is a fusion protein, in which the N-terminus and C-terminus of the Epac polypeptide are fused to the RLuc and GFP. For example, the fusion protein can comprise the amino acid sequence of SEQ ID NO:3.

In some examples, the Epac polypeptide is a truncated mutant, which lacks the N-terminal fragment corresponding to residues 1-147 of SEQ ID NO:1. Alternatively or in addition, the Epac polypeptide contains point mutations T781A and F782A as compared to a wild-type counterpart. In one example, the Epac polypeptide comprises the amino acid sequence of SEQ ID NO:2.

In some embodiments, the cell in the assay system can be a mammalian cell, e.g., an insulin-secreting cell.

Also within the scope of the present disclosure is a method for determining an intracellular cAMP level, comprising (i) culturing a cell that expresses a cAMP sensor, which is a protein complex comprising an Epac polypeptide, a RLuc (e.g., RLuc8), and GFP (e.g., GFP2); (ii) adding to the cultured cell a substrate of the RLuc (e.g., DEEP BLUE C); (iii) measuring a first luminescent signal at a wave length of around 370-450 nm (e.g., 395 nM) and a second luminescent signal at a wave length of 500-530 nm (e.g., 510 nM); and (iv) determining the intracellular cAMP level in the cell based on a ratio of the second luminescent signal to the first luminescent signal (the second luminescent signal at a wave length of 500-530 nm/the first luminescent signal at a wave length of around 370-450 nm).

In some embodiments, the cAMP biosensor is a fusion protein, in which the N-terminus and C-terminus of the Epac polypeptide are fused to the RLuc and GFP. For example, the fusion protein can comprise the amino acid sequence of SEQ ID NO:3. The Epac polypeptide can be a truncated mutant, which lacks the N-terminal fragment corresponding to residues 1-147 of SEQ ID NO:1. Alternatively or in addition, the Epac polypeptide contains point mutations T781A and F782A as compared to a wild-type counterpart. In one example, the Epac polypeptide comprises the amino acid sequence of SEQ ID NO:2.

In some embodiments, the cell, which can be a mammalian cell, is prepared by introducing into a host cell one or more nucleic acids encoding the Epac polypeptide, the RLuc, and the GFP, wherein the one or more nucleic acids are in operable linkage to a suitable promoter. In one example, the cell is a mammalian cell capable of secreting insulin.

Further, the present disclosure features a method for identifying an agent capable of regulating the level of intracellular cAMP, comprising: (i) providing a cell that expresses a cAMP sensor, which is a protein complex comprising an Epac polypeptide, a RLuc (e.g., RLuc8), and a GFP (e.g., GFP2); (iii) contacting the cell with a candidate agent in the presence of a substrate of the RLuc; (iv) measuring a first luminescent signal at a wave length of around 370-450 nm and a second luminescent signal at a wave length of 500-530 nm; (v) calculating a ratio between the first luminescent signal and the second luminescent signal; and (vi) determining whether the candidate agent is capable of regulating the level of intracellular cAMP in the cell; wherein the ratio differs from that in the absence of the candidate agent indicates that the candidate agent regulates the level of intracellular cAMP in the cell.

In particular embodiments, the method of the method for identifying an agent capable of regulating the level of intracellular cAMP according to the present invention includes the following steps:

(i) conducting a first assay, including culturing a cell expressing a cAMP sensor as described herein in the presence of a candidate agent, adding a substrate of RLuc, measuring a first luminescent signal at a wave length of around 370-450 nm and a second luminescent signal at a wave length of 500-530 nm, and obtaining a first ratio of the second luminescent signal to the first luminescent signal (the second luminescent signal/the first luminescent signal);

(ii) conducting a second assay, including culturing a cell expressing a cAMP sensor as described herein in the absence of a candidate agent, adding a substrate of RLuc, measuring a third luminescent signal at a wave length of around 370-450 nm and a fourth luminescent signal at a wave length of 500-530 nm, and obtaining a second ratio of the fourth luminescent signal to the third luminescent signal (the fourth luminescent signal/the third luminescent signal); and (iii) comparing the first ratio and the second ratio, and determining whether the candidate agent is capable of regulating the level of intracellular cAMP in the cell, wherein the first ratio differs from the second ratio indicates that the candidate agent regulates the level of intracellular cAMP in the cell.

In particular, if the first ratio is lower than the second ratio, the candidate agent is determined as a stimulator to enhance the intracellular cAMP level; and in the contrast, if first ratio is higher than the second ratio, the candidate agent is determined as an inhibitor to reduce the intracellular cAMP level.

In some embodiments, the cAMP biosensor is a fusion protein, in which the N-terminus and C-terminus of the Epac polypeptide are fused to the RLuc and GFP. For example, the fusion protein can comprise the amino acid sequence of SEQ ID NO:3.

In some embodiments, the first luminescent is measured at the wave length of 395 nm and the second luminescent is measured at the wave length of 510 nm.

Also described herein are a nucleic acid, comprising a nucleotide sequence encoding a fusion protein (e.g., SEQ ID NO:3) that comprises an Epac polypeptide, a RLuc, and a GFP, wherein the N-terminus and C-terminus of the Epac are fused to the RLuc and GFP; a vector such as an expression vector comprising such a nucleic acid, and a host cell comprising the vector.

Another aspect of the invention relates to methods for controlling blood glucose levels. Further, the invention feature methods for treating a disease or condition characterized by increased expression levels or biological activity of GLP-1R in a subject in need thereof, comprising administering to the subject an effective amount of an endocannabinoid-like compound or a pharmaceutical composition as described herein.

A method in accordance with the invention includes administering to a subject in need thereof a composition comprising an endocannabinoid-like compound. In some embodiments, the compound may be oleoylethanolamide (OEA) or 2-oleoylglycerol (2-OG). The method may further include administering to the subject a GLP-1 receptor ligand. The GLP-1 receptor ligand may be GLP-1. The compound and the GLP-1 receptor ligand may be administered sequentially or simultaneously. In certain embodiments, GLP-1 is endogenous. In certain embodiments, GLP-1 is exogenous.

The composition of the present invention can be effectively used as a pharmaceutical or food composition for prevention and alleviation of a disease or condition associated with GLP-1R. Examples of the method of the invention include, but not limited to, prevention and alleviation of diabetes, alleviation of heart diseases, alleviation of arteriosclerosis, alleviation or treatment of digestive disorders and malabsorption, anti-obesity or appetite suppression, neuroprotective effects, treatment or alleviation of liver diseases or the like.

In some embodiments, the endocannabinoid-like compound is administered at an amount effective to bind to GLP-1 to enhance activation of GLP-1R signaling pathway.

The details of one or more embodiments of the invention are set forth in the description below. Other features or advantages of the present invention will be apparent from the following drawings and detailed description of several embodiments, and also from the appended claims. FIGURE

BRIEF DESCRIPTION OF THE DRAWINGS

(FIG. 1A) Overlap extension PCR to generate Rluc8-Epac1$_{148-430}$pcDNA* encoding Epac1 amino acids 148-430 (SEQ ID NO: 8). (FIG. 1B) Generation of Rluc8-Epac1$_{148-881}$pcDNA* encoding Epac1 amino acids 148-881 (SEQ ID NO: 7). (FIG. 1C) Generation of construct encoding the three-protein fusion of Rluc8-Epac1$_{148-881(T781A,F782A)}$-GFP2 (RG-cAMP sensor) containing Epac1 sequence encoding amino acids 148-881, where Thr781 and Phe782 in the Epac 1 have been changed to alanine.

(FIG. 2A) Schematic diagram of RG-cAMP sensor stably expressed in RINm5F cells and comprising Epac1 (amino acids 148-881 with point mutations T781A and F782A) fused between the Rluc8 (1-311) and GFP2 (1-239) proteins with LeuGlyLeu and AlaThr as linkers between Rluc8 and Epac1$_{148-881(T781A, F782A)}$ and GFP2, respectively. (FIG. 2B) Reduction in BRET ratio in response to titration of the membrane-permeable cAMP analog 8-Br-2'-OMe-cAMP-AM in RINm5F cells stably expressing the RG-cAMP sensor. (FIG. 2C) BRET responses to increasing concentration of adenylyl cyclase activator forskolin in the (■) presence and (●) absence of 250 µM adenylyl cyclase inhibitor MDL-12330A. Data are mean±standard error of the mean (SE) of triplicate assays of three independent experiments.

FIG. 3A-3C shows the cAMP responses to titration of GLP-1 (7-36) (SEQ ID NO: 9) amide, gastric inhibitory polypeptide (GIP), and glucagon in RINm5F cells stably expressing RG-cAMP sensor. Dose response of cAMP production to; (FIG. 3A) Titration of GLP-1 (7-36) amide in the (●) absence and (■) presence of 500 nM exendin 9 (Ex-9). (FIG. 3B) Titration of GIP in the (●) absence and (■) presence of 5 uM GIP(8-42) (SEQ ID NO: 14). (FIG. 3C) Titration of glucagon in the (●) absence and (■) presence of 100 uM [des-H1, E9]-glucagon amide. Data are mean±standard error of the mean (SE) of triplicate assays from three independent experiments.

(FIG. 4A) With (■) 106.2 and (▲) 10.6 uM OA and (●) vehicle. (FIG. 4B) With (■) 107 and (▲) 10.7 uM LA and (●) vehicle. (FIG. 4C) With indicated concentration of (■) SA, (▲) ALA, (▼) γ-LA, and (●) vehicle. (FIG. 4D) With indicated concentration of (♦) SEA, (▲) PEA, and (●) vehicle only; and (FIG. 4E) with 72 uM (■) ODA and (●) vehicle only. Data are mean±standard error of the mean (SE) of triplicate assays from at least two independent experiments.

FIG. 5A-5E shows the OEA and 2-OG enhance GLP-1 (7-36) amide-stimulated cAMP productions in RINm5F cells. FIG. 5A and FIG. 5B) cAMP production in response to dose titration of GLP-1 (7-36) amide (●) alone or in the presence of indicated concentration of (FIG. 5A) OEA and (FIG. 5B) 2-OG. (C-D), Titration of exendin 4 for cAMP production in the presence of indicated concentration of (FIG. 5C) OEA and (FIG. 5D) 2-OG. (FIG. 5E) cAMP production in response to 200 μM of GLP-1 (7-36) amide alone or in the presence of 500 nM exendin-9 (Ex-9) and indicated concentration of OEA and 2-OG. Data are mean±standard error of the mean (SE) of triplicate assays from three independent experiments.

FIG. 6A-6D shows the binding of GLP-1 to OEA, 2-OG and SEA. (FIG. 6A) Sequence of His-tagged GLP-1 (7-36) (SEQ ID NO: 6), six consecutive histidine residues is tagged to the C-terminal of GLP-1 (7-36) peptide. (FIG. 6B) Binding of 0.2 uM $^3$H-OEA to increasing concentrations of His-tagged GLP-1 (7-36). (FIG. 6C) Binding of 0.1 uM His-tagged GLP-1 (7-36) to increasing concentration of $^3$H-OEA. (FIG. 6D) Competition of 2-OG and SEA for the binding of 0.2 uM OEA to 0.2 uM His-tagged GLP-1 (7-36). Binding reactions, separation of His-tagged GLP-1 (7-36) bound $^3$H-OEA and free $^3$H-OEA, quantitation of specific bound $^3$H-OEA were described in Experimental Procedures. Data points represent the average of triplicate determinations from three independent experiments.

(FIG. 7C) Specific binding of $^{125}$I-GLP-1(7-36) to GLP-1R-V2R membrane in the (●) absence or (■) presence of 9.2 uM of OEA. Binding reactions (220 uL) were carried out in the absence (Total Binding) or presence (Non-specific Binding) of 500-fold excess unlabeled exendin 4, separation of bound and free $^{125}$I-GLP-1(7-36) and calculation of specific binding are described in Experimental Procedures. Specific binding was determined by subtracting nonspecific binding from total binding. The data shown are the average of three independent experiments performed in duplicate. Data were fitted globally to a one-site saturation isotherm.

(FIG. 8A) GLP-1 (7-36) (SEQ ID NO: 9) amide and potential trypsin cleavage fragments, GLP-1 (7-26) (SEQ ID NO: 11) and GLP-1(7-34) (SEQ ID NO: 10). (FIG. 8B) Cleavage of substrate by 0.000125% trypsin was assayed in the (■) presence and (○) absence of 92 uM OEA. Extent of cleavage was monitored by real-time reading of optical density (OD) at 405 nm (see Experimental Procedures). (C and D) cAMP production in response to residual GLP-1 (7-36) amide after inactivation by indicated concentration of trypsin in the (FIG. 8C) absence or (FIG. 8D) presence of 92 uM OEA. (FIG. 8E and FIG. 8F) cAMP production in response to residual GLP-1 (7-36) amide after inactivation by 0.00067% trypsin in the presence of indicated concentration of (FIG. 8E) OEA or (FIG. 8F) SEA. All the activity assays were carried in the presence of 9.2 uM of OEA, except (FIG. 8F) where cAMP assays were carried out in the presence of 9.2 uM of SEA, All data are mean±standard error of the mean (SE) of duplicate assays from three independent experiments.

DETAILED DESCRIPTION OF THE INVENTION

Figure 1A:
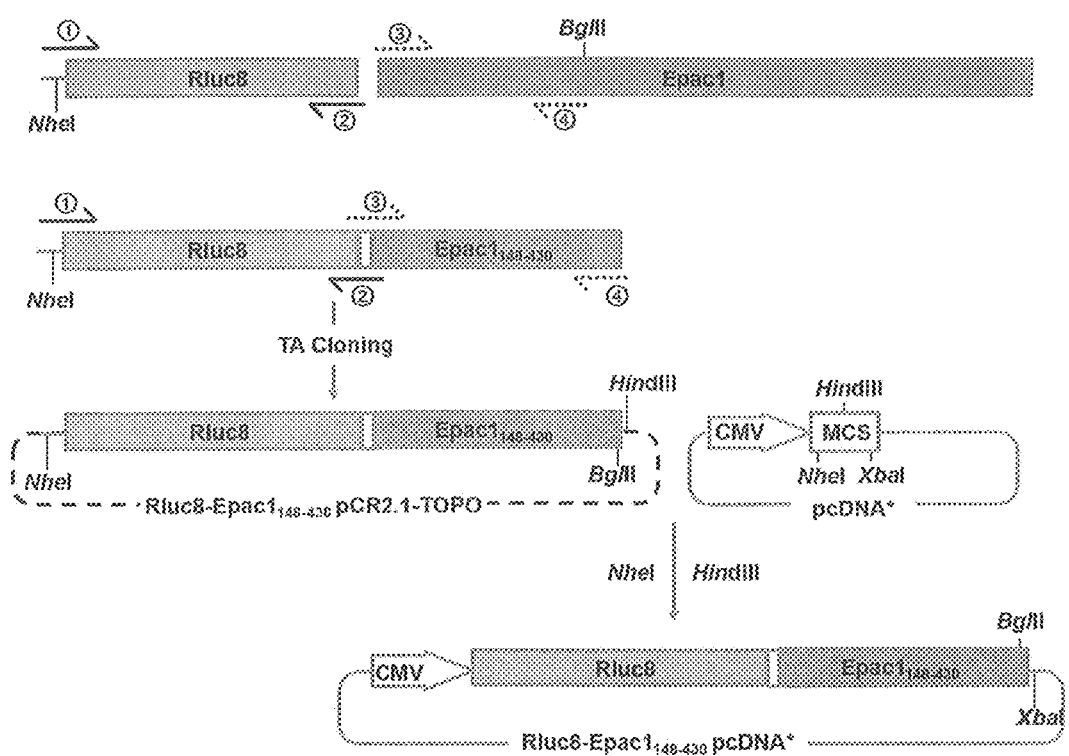
FIG. 1A-1C show the generation of construct to express fusion protein RG-cAMP sensor.

Described herein is a cAMP biosensor allowing for real-time detection of intracellular cAMP levels and the uses thereof in measuring cAMP levels and identifying agents capable of regulating cAMP production, such as agents that modulate a GPGR-mediated (e.g., GLP-1/GLP-1 receptor-mediated) signaling pathway. Also, described herein is a method for controlling blood glucose levels, and a method for treating a disease or condition characterized by increased expression levels or biological activity of GLP-1R in a subject in need thereof. The methods comprise administering to the subject an effective amount of an endocannabinoid-like compound or a pharmaceutical composition as described herein.

1. cAMP Biosensor

The cAMP biosensor described herein is a protein complex (e.g., a fusion protein) comprising an exchange protein activated by cAMP (Epac) polypeptide, a *Renilla* luciferase (RLuc), and a green fluorescent protein (GFP). Bioluminescence resonance energy would be efficiently transferred (BRET) from the donor (RLuc8) to acceptor (GFP) when the two molecules are in close vicinity. The biosensor BRET signal can be determined by calculating the ratio of the light emitted at 500 to 520 nm to the light emitted at 390 to 410 nm (BRET ratio). When the Epac polypeptide binds cAMP, it induces a conformational change of the cAMP biosensor, leading to the increase of distance between RLuc 8 and GFP and thus, the decrease of the BRET signal (the BRET ratio). FIG. 1 illustrates an exemplary cAMP biosensor described herein and the conformational change upon binding of cAMP to the Epac polypeptide therein.

A protein complex as described herein refers to a composite unit that is a combination of at least the three polypeptide components described herein (RLuc, Epac, and GFP) formed by interaction among the polypeptide components. A protein complex can be formed by the binding of each of the two polypeptide components through covalent or non-covalent binding affinities. For example, two interacting partners can be covalently crosslinked or form a fusion protein so that the protein complex becomes more stable.

In some embodiments, the cAMP biosensor described herein comprises a fusion protein, in which the Epac polypeptide is fused to the RLuc and GFP at its N-terminus and C-terminus. In one example, the fusion protein comprises, from the N-terminus to the C-terminus, the RLuc, the Epac polypeptide, and the GFP. In another example, the fusion protein comprises, from the N-terminus to the C-terminus, the GFP, the Epac polypeptide, and the RLuc.

In some embodiments, the RLuc and Epac polypeptide, and the GFP and Epac polypeptide, are fused via a peptide linker, e.g., peptide LGL and peptide AT. In one example, the RLuc is fused to the N-terminus of the Epac polypeptide via peptide LGL. In another example, the GFP is fused to the C-terminus of the Epac polypeptide via peptide AT. In one example, the cAMP biosensor is a fusion protein comprising the amino acid sequence shown below (SEQ ID NO:3):

MASKVYDPEQRKRMITGPQWWARCKQMNVLDSFINYYDSEKHAENAVIFL

HGNATSSYLWRHVVPHIEPVARCIIPDLIGMGKSGKSGNGSYRLLDHYKY

LTAWFELLNLPKKIIFVGHDWGAALAFHYAYEHQDRIKAIVHMESVVDVI

ESWDEWPDIEEDTALIKSEEGEKMVLENNFFVETVLPSKIMRKLEPEEFA

AYLEPFKEKGEVRRPTLSWPREIPLVKGGKPDVVQIVRNYNAYLRASDDL

PKLFIESDPGFFSNAIVEGAKKFPNTEFVKVKGLHFLQEDAPDEMGKYIK

SFVERVLKNEQLGLEPVGTHEMEEELAEAVALLSQRGPDALLTVALRKPP

GQRTDEELDLIFEELLHIKAVAHLSNSVKRELAAVLLFEPHSKAGTVLFS

QGDKGTSWYIIWKGSVNVVTHGKGLVTTLHEGDDFGQLALVNDAPRAATI

```
ILREDNCHFLRVDKQDFNRIIKDVEAKTMRLEEHGKVVLVLERASQGAGP

SRPPTPGRNRYTVMSGTPEKILELLLEAMGPDSSAHDPTETFLSDFLLTH

RVFMPSAQLCAALLHHFHVEPAGGSEQERSTYVCNKRQQILRLVSQWVAL

YGSMLHTDPVATSFLQKLSDLVGRDTRLSNLLREQWPERRRCHRLENGCG

NASPQMKARNLPVWLPNQDEPLPGSSCAIQVGDKVPYDICRPDHSVLTLQ

LPVTASVREVMAALAQEDGWTKGQVLVKVNSAGDAIGLQPDARGVATSLG

LNERLFVVNPQEVHELIPHPDQLGPTVGSAEGLDLVSAKDLAGQLTDHDW

SLFNSIHQVELIHYVLGPQHLRDVTTANLERFMRRFNELQYWVATELCLC

PVPGPRAQLLRKFIKLAAHLKEQKNLNSFFAVMFGLSNSAISRLAHTWER

LPHKVRKLYSALERLLDPSWNHRVYRLALAKLSPPVIPFMPLLLKDMAAI

HEGNHTLVENLINFEKMRMMARAARMLHHCRSHNPVPLSPLRSRVSHLHE

DSQVARISTCSEQSLSTRSPASTWAYVQQLKVIDNQRELSRLSRELEPAT

_MVSKGEELFTGVVPILVELDGDVNGHKFSVSGEGEGDATYGKLTLKFICT_

_TGKLPVPWPTLVTTLSYGVQCFSRYPDHMKQHDFFKSAMPEGYVQERTIF_

_FKDDGNYKTRAEVKFEGDTLVNRIELKGIDFKEDGNILGHKLEYNYNSHN_

_VYIMADKQKNGIKVNFKIRHNIEDGSVQLADHYQQNTPIGDPVLLPDNH_

_YLSTQSALSKDPNEKRDHMVLLEFVTAAGITLGMDELYK_
```

The N-terminal italicized region refers to the RLuc8 portion, the C-terminal italicized and underlined region refers to GFP portion, and the middle region refers to the Epac portion. The fragments in boldface are linkers between RLuc8 and Epac and between Epac and GFP. The AA fragment in boldface and underlined refers to the point mutations in the Epac portion.

1.1 Epac Polypeptide

Exchange proteins directly activated by cyclic AMP (Epacs) represent a family of cAMP-binding effector proteins, which are well known in the art. The Epac polypeptide can be encoded by Epac1 or Epac2 gene. In some embodiments, the Epac polypeptide is a wild-type protein derived from a suitable origin, e.g., human, primate, mouse, rat, etc.

In one example, the Epac polypeptide has an amino acid sequence set forth as SEQ ID NO:1 shown below (*Homo sapiens*):

```
MVLRRMHRPRSCSYQLLLEHQRPSCIQGLRWTPLTNSEESLDFSESLEQA

STERVLRAGRQLHRHLLATCPNLIRDRKYHLRLYRQCCSGRELVDGILAL

GLGVHSRSQVVGICQVUDEGALCHVKHDWAFQDRDAQFYRFPGPEPEPVG

THEMEEELAEAVALLSQRGPDALLTVALRKPPGQRTDEELDLIFEELLHI

KAVAHLSNSVKRELAAVLLFEPHSKAGTVLFSQGDKGTSWYTIWKGSVNV

VTHGKGLVTTLHEGDINGQLALVNDAPRAATIILREDNCHFLRVDKQDFN

RIIKDVEAKTMRLEEHGKVVLVLERASQGAGPSRPPTPGRNRYTVMSGTP

EKILELLLEAMGPDSSAHDPTETFISDFLLTHRVEMPSAQLCAALLHHFH

VEPAGGSEQERSTYVCNKRQQILRLVSQWVALYGSMLHTDPVATSFLQKL

SDLVGRDTRLSNLLREQWPERRRCHRLENGCGNASPQMKARNLPVWLPNQ

DEPLPGSSCAIQVGDKVPYDICRPDHSVLTLQLPVTASVREVMAALAQED

GWTKGQVLVKVNSAGDAIGLQPDARGVATSLGLNERLFVVNPQEVHELIP

HPDQLGPTVGSAEGLDLVSAKDLAGQLTDHDWSLFNSIHQVELIHYVLGP

QHLRDVTTANLERFMRRFNELQYWVATELCLCPVPGPRAQLLRKFIKLAA

HLKEQKNLNSFFAVMFGLSNSAISRLAFITWERLPHKVRKLYSALERLLD

PSWNHRVYRLALAKLSPPVIPFMPLLLKDM_TF_IHEGNHTLVENLINFEKM

RMMARAARMLHHCRSHNPVPLSPLRSRVSHLHEDSQVARISTCSEQSLST

RSPASTWAYVQQLKVIDNQRELSRLSRELEP
```

In another example, the Epac polypeptide is a wild-type protein that shares at least 85% (e.g., 90%, 95%, or 97%) sequence identity as SEQ ID NO:1. Such wild-type Epac proteins are known in the art and can be identified from a protein database such as GenBank using SEQ ID NO:1 as a query. Examples of wild-type Epac polypeptides for use in making any of the cAMP biosensors described herein include, but not limited to, those described under GenBank accession numbers NP_006096.2, AAH92404.2, XP_004053058.1, XP_002752134.1, XP_006916911.1, XP_005206450.1, XP_006520941.1, XP_006242414.1, NP_001171282.1, XP_005611178.1, and XP_004638650.1.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Alternatively, the Epac polypeptide in the cAMP biosensor can be a functional variant of a wild-type Epac (e.g., SEQ ID NO:1). In some embodiments, the Epac polypeptide is a truncation mutant, e.g. SEQ ID NO: 7, which lacks an N-terminal fragment (e.g., the N-terminal fragment corresponding to residues 1-147 of SEQ ID NO:1) as compared to the wild-type counterpart. In other embodiments, the Epac polypeptide contains mutations that lead to inactivation of its guanine nucleotide exchange activity. Such mutations include point mutations at one or more positions corresponding to positions T781 and F782 in SEQ ID NO:1. For example, the T and F residues can be replaced with A. In one example, the Epac polypeptide comprises SEQ ID NO:2 shown below:

```
EPVGTHEMEEELAEAVALLSQRGPDALLTVALRKPPGQRTDEELDLIFEE

LLHIKAVAHLSNSVICRELAAVLLFEPHSKAGTVLESQGDKGTSWYIIWK

GSVNVVTHGKGLVTTLHEGDDFGQLALVNDAPRAATIILREDNCHFLRVD

KQDFNRIIKDVEAKTMRLEEHGKVVLVLERASQGAGPSRPPTPGRNRYTV

MSGTPEKILELLLEAMGPDSSAHDPTETFLSDFLLTHRVFMPSAQLCAAL

LHHFHVEPAGGSEQERSTYVCNKRQQILRLVSQWVALYGSMLHTDPVATS

FLQKLSDLVGRDTRLSNLLREQWPERRRCHRLENGCGNASPQMKARNLPV
```

-continued
WLPNQDEPLPGSSCAIQVGDKVPYDICRPDHSVLTLQLPVTASVREVMAA

LAQEDGWTKGQVLVKVNSAGDAIGLQPDARGVATSLGLNERLFVVNPQEV

HELIPHPDQLGPTVGSAEGLDLVSAKDLAGQLTDHDWSLFNSIHQVELIH

YVLGPQHLRDVTTANLERFMRRFNELQYWVATELCLCPVPGPRAQLLRKF

IKLAAHLKEQKNLNSFFAVMFGLSNSAISRLAHTWERLPHKVRKLYSALE

RLLDPSWNHRVYRLALAKLSPPVIPFMPLLLKDMAAIHEGNHTLVENLIN

FEKMRMMARAARMLHHCRSHNPVPLSPLRSRVSFILHEDSQVARISTCSE

QSLSTRSPASTWAYVQQLKVIDNQRELSRLSRELEP

1.2 Renilla Luciferase (RLuc)

A *Renilla* luciferase is a luciferase derived from sea pansy (e.g., *Renilla reniformis*), which catalyzes the reaction of:

coelenterazine+O2→coelenteramide+CO2+photon of light

In some embodiments, the RLuc used in the cAMP biosensor described herein is a wild-type lucerifase, for example, RLuc8, which may comprise the following amino acid sequence (SEQ ID NO:4) (*Renilla reniformis*) shown below:

MASKVYDPEQRKRMITGPQWWARCKQMNVLDSFINYYDSEKHAENAVIFL

HGNATSSYLWRHVVPHIEPVARCIIPDLIGMGKSGKSGNGSYRLLDHYKY

LTAWFELLNLPKKIIFVGHDWGAALAFHYAYEHQDRIKAIVHMESVVDVI

ESWDEWPDIEEDIALIKSEEGEKMVLENNFFVETVLPSKIMRKLEPEEFA

AYLEPFKEKGEVRRPTLSWPREIPLVKGGKPDVVQIVRNYNAYLRASDDL

PKLFIESDPGFFSNAIVEGAKKFPNTEFVKVKGLHFLQEDAPDEMGKYIK

SFVERVLKNEQ

RLuc enzymes for use in the cAMP biosensor described herein may be other wild-type RLuc known in the art, which may share high sequence homology with SEQ ID NO:4 (e.g., at least 85%, 90%, 95%, or 95% sequence identity). Examples include, but are not limited to, those described under GenBank accession numbers ADF42668.1, AA048595.1, AAF93166.1, and AAG54094.1. Other RLuc proteins can be identified from a protein database such as GenGank using SEQ ID NO:4 as a query.

1.3 Green Fluorescent Protein (GFP)

A green fluorescent protein (GFP) is a protein that exhibits bright green fluorescence when exposed to light in the blue to ultraviolet range. GFP for use in the instant disclosure can be derived from a suitable natural source, such as a marine organism, e.g., jellyfish (*Aequorea victoria*) or sea pansy (*Renilla reniformis*). In one example, the GFP comprises the amino acid sequence of SEQ ID NO:5 (*Aequorea victoria*) shown below:

MVSKGEELFTGVVPILVELDGDVNGHKFSVSGEGEGDATYGKLTLKFICT

TGKLPVPWPTLVTTLSYGVQCFSRYPDHMKQHDFFKSAMPEGYVQERTIF

FKDDGNYKTRAEVKFEGDTLYNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK

Other GFP proteins (e.g., GFP2) and GFP derivatives (e.g., the S65T mutant) known in the art are also within the scope of the present disclosure. In some instance, such GFP polypeptides can share a high sequence identity to SEQ ID NO:5 (e.g., at least 85%, 90%, 95%, or 97% identical to SEQ ID NO:5).

The cAMP biosensor disclosed herein can be prepared by any methods known in the art. For example, the three components (Epac polypeptide, RLuc, and GFP) may be prepared separately via routine recombinant technology or via purification from a natural source and then conjugated via conventional practice, e.g., protein crosslinking.

When the cAMP biosensor is a fusion protein, it can be prepared by, e.g., conventional recombinant technology. For example, a nucleic acid encoding the fusion protein can be inserted into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art.

A variety of promoters can be used for expression of the fusion protein described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell*, 49:603-612 (1987)], those using the tetracycline repressor (tetR) [Gossen, M., and Bujard, H., *Proc. Natl. Acad. Sci. USA* 89:5547-5551 (1992); Yao, F. et al., Human Gene Therapy, 9:1939-1950 (1998); Shockelt, P., et al., *Proc. Natl. Acad Sci. USA*, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell*, 49:603-612 (1987)]; Gossen and Bujard (1992); [M. Gossen et al., *Natl. Acad Sci. USA*, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy*). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., *Proc. Natl. Acad Sci. USA*, 92:6522-6526 (1995)), to achieve its regulatable effects.

Examples of polyadenylation signals useful to practice the methods described herein include, but are not limited to, human collagen I polyadenylation signal, human collagen II polyadenylation signal, and SV40 polyadenylation signal.

The fusion protein biosensor described herein can be produced in bacterial cells, e.g., *E. coli* cells. Alternatively, they can be produced in eukaryotic cells. In one embodiment, the fusion protein is expressed in a yeast cell such as *Pichia* (see, e.g., Powers et al., 2001, *J. Immunol. Methods.* 251:123-35), *Hanseula*, or *Saccharomyces*. In another embodiment, the fusion protein can be produced in mammalian cells, such as mammalian cells that are capable of secreting insulin. Mammalian host cells for expressing the fusion protein include, but are not limited to, Chinese Hamster Ovary (CHO cells) (including dhfr-CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, and a cell from a transgenic animal, e.g., a transgenic mammal. For example, the cell is a mammary epithelial cell.

In an exemplary system for recombinant expression of a fusion protein as described herein, a recombinant expression vector encoding the fusion protein is introduced into dhfr⁻ CHO cells by calcium phosphate-mediated transfection. Within the recombinant expression vector, the nucleotide sequence encoding the fusion protein can be operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the fusion protein, which can then be recovered from the culture medium.

Standard molecular biology techniques are used to prepare the recombinant expression vector, transfect the host cells, select for transformants, culture the host cells and recover the fusion protein from the culture medium. For example, some antibodies can be isolated by affinity chromatography.

Figure 2A:
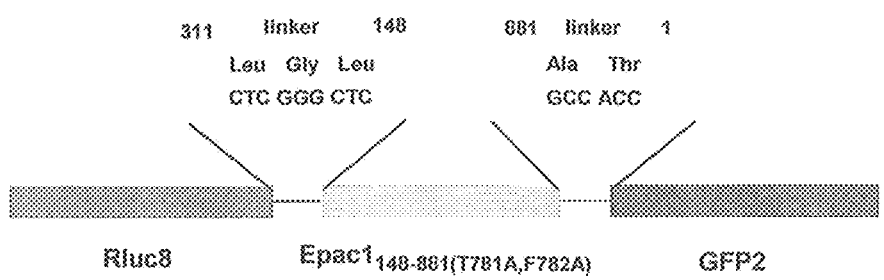
FIG. 2A-2C show the detection of intracellular cAMP by RG-cAMP sensor in RINm5F cells.

2. Application of cAMP Biosensor in Determining cAMP Levels and Screening for Desirable Modulators The cAMP biosensor described herein allows for real-time detection of cAMP, particularly intracellular cAMPs. As shown in FIG. 2, the luminescent signal released from the donor (RLuc) is at a wave length of around 370-450 (e.g., 395 nM) does not overlap with the luminescent signal released from the acceptor (GFP) at a wave length of 500-530 nm (e.g., 510). Thus, the BRET technology described herein, which involves the cAMP biosensor also described herein, would unexpectedly yield more accurate results with high sensitivity as compared with the BRET technology known in the art.

Also described herein are the uses of the cAMP biosensor described herein for determining cAMP levels, both in vitro and in vivo (cell based) and for identifying agents capable of modulating a OPGR-mediated signaling pathway, which lead to the changes of intracellular cAMP production.

The cAMP biosensor described herein comprises a Epac (e.g., Epac1 or Epac2) polypeptide, a RLuc protein, and a GFP protein. The Epac polypeptide is a potent cAMP binding protein and when conjugated (e.g., fused) at its N-terminus and C-terminus with an energy donor RLuc protein (e.g., Rluc8) and an energy acceptor fluoroprotein (GFP such as GFP2), cAMP binding will result in conformational changes in the cAMP biosensor, which would lead to the reduction of the energy transfer from RLuc to GFP and thus the reduction of the BRET ratio. Accordingly, the cAMP biosensor described herein can be used in determining the cAMP level in a sample, including intracellular cAMP levels. The cAMP biosensor can also be used in identifying agents capable of modulating cAMP production, such as agents capable of modulating GPGR-mediated signaling pathway.

2.1 Determination of cAMP Levels

In some embodiments, the cAMP biosensor can be used in methods for detecting the presence or measuring the level of cAMP in a sample, which can be a biological sample obtained from a subject (e.g., a human patient). To perform such a method, the cAMP biosensor can be incubated with a sample suspected of containing cAMP in the presence of a RLuc substrate (e.g., a coelenterazine compound) for a suitable period of time under suitable conditions allowing for the binding of cAMP to the Epac polypeptide in the biosensor. Any RLuc substrates, which are well known in the art, can be used in the methods described herein. The cAMP sensor can then be subjected to measurement of a first a first luminescent signal at a wave length of around 370-450 nm (e.g., 395 nM) and a second luminescent signal at a wave length of 500-530 nm (e.g., 510 nM). A ratio between the first luminescent signal and the second luminescent signal (BRET ratio) can then be calculated. If the BRET ratio decreases as compared to the BRET ratio in the absence of cAMP, it indicates that the sample contains cAMP. The level of cAMP in the sample can be determined based on the BRET ratio of the biosensor after binding to cAMP.

In addition, the cAMP biosensor can also be used in methods for determining intracelluar cAMP levels. For example, the cAMP biosensor can be introduced into a target cell, which can be a mammalian cell, e.g., a mammalian cell capable of secreting insulin. In one example, an expression vector for expressing a fusion protein of the cAMP biosensor can be introduced into the target cell. Positive transformants, which stably express the fusion protein can be selected via routine technology. The selected cells that express the fusion protein can then be incubated in a suitable medium containing a RLuc substrate such as any of those described herein under suitable conditions for a suitable period of time. Afterwards, the cells are examined to measure a first a first luminescent signal at a wave length of around 370-450 nm (e.g., 395 nM) and a second luminescent signal at a wave length of 500-530 nm (e.g., 510 nM). A BRET ratio is calculated accordingly. By comparing the BRET ratio with a control value, the presence level of intracellular cAMP can be determined. The control value can be a BRET ratio in the absence of cAMP. In that case, if the BRET ratio of the cell that expresses the fusion protein is lower than the control level, it indicates that the cell contains cAMP. Alternatively, the control value can be a BRET value determined in the presence of cAMP of a predetermined level. If the BRET ratio of the cell deviates from the control value, it indicates that the intracellular cAMP level of the cell is higher or lower than the predetermined level.

2.2 Screening for Desirable Agents

The cAMP biosensor described herein can also be used in a method for identifying agents that modulates a GPOR-mediated signaling pathway, using intracellular cAMP production as a read out. In one example, the method described herein is used to identify modulators of the GLP-1 receptor signaling pathway. Such modulators may be useful in treating diabetes and other disorders associated with dysregulation of the GLP-1 receptor signaling pathway.

In some embodiments, an assay system comprising a cell capable of expressing a cAMP biosensor such as a fusion protein as described herein can be constructed via routine technology. The cell can be a mammalian cell capable of secreting insulin, e.g., RINm5F cells. A candidate agent can be incubated with the cell expressing the cAMP biosensor in the presence of a RLuc substrate under suitable conditions allowing for the binding of intracellular cAMP to the biosensor for a suitable period of time. When necessary, the cell can be incubated with a known regulator as a positive control or incubated with a mock agent as a blank control. The cells can then be examined to determine a first luminescent signal at a wave length of around 370-450 nm (e.g., 395 nM) and a second luminescent signal at a wave length of 500-530 nm (e.g., 510 nM). A BRET ratio can be determined accordingly. By comparing the BRET ratio with that of the blank control and/or the positive control, the candidate agent can be assessed to determine whether it is a modulator of a GPRP-mediated signaling pathway (e.g., a modulator of the GLP-1 receptor signal pathway).

As shown in the Examples below, the cAMP biosensor was used successfully to determine intracellular cAMP production in cells in the presence of GLP-1, a ligand of GLP-1 receptor that triggers a GPRP-mediated signaling pathway. As also shown in the Examples below, the cAMP biosensor system described herein was used successfully to identify certain fractions obtained from a plant extract as displaying the activity to potentiate the GLP-1-mediated signaling pathway.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

2.3 Activation of GLP-1 Receptor Activity with Endocannabinoid-Like Lipids in Presence of GLP-1

In some embodiments, the endocannabinoid-like lipid as used herein is oleoylethanolamide (OEA) or 2-oleoylglycerol (2-OG).

The endocannabinoid-like lipid can be used in the method for treating a disease or condition associated with GLP-1R signaling.

In some embodiments, the endocannabinoid-like lipid is administered to treat a disease or condition associated with GLP-1R signaling in a subject in need, at an amount effective to bind to GLP-1 to enhance the GLP-1R signaling.

In some embodiments, the effective amount of OEA or 2-OG is lower than that of other 18-carbon fatty acid or their derivatives, such as oleic acid (OA; 18:1), linoleic acid (LA; 18:2), palmitoylethanolamide (PEA), or n-oleoyldopamine (ODA). In some examples, the amount of OEA or 2-OG is 90% or less (e.g. 80%, 70%, 60%, 50%, 40%, 30%, 20%, 10%) of the amount of OA, LA, PEA or ODA to achieve a desired effect, e.g. enhancement of GLP-1R signaling.

The term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder.

The term "effective amount" used herein refers to the amount of an active ingredient to confer a desired biological effect in a treated subject, for example, enhancement of cAMP response or GLP-1 signaling or reduction of blood glucose level.

In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

The present invention is further illustrated by the following examples, which are provided for the purpose of demonstration rather than limitation.

Examples

1. Experimental Procedures

Reagents—

A U2OS osteosarcoma cell line stably expressing a β-arrestin2:GFP fusion protein was obtained from Norak Biosciences (Morrisville, N.C., USA) (now Molecular Devices, a part of MDS, Mississauga, ON, Canada). The construct pcDNA-Rluc8, which expresses a variant of Renilla luciferase (Rluc8) (20) and a green fluorescent protein (GFP2), cDNA were kind gifts of Drs. Sanjiv Gambhir (Stanford University, Stanford, Calif., USA) and Szu-Hao Kung (21), respectively. cDNA encoding human exchange protein activated by cAMP 1 (Epac1; Rap guanine nucleotide exchange factor 3) and cDNA of human GLP-1R were purchased from OriGene Technologies (Rockville, Md., USA). All oligonucleotides were from Mission Biotech (Taipei, Taiwan). The Lipofectamine LTX Transfection Kit and TOPO TA Cloning Kit were from Invitrogen (Carlsbad, Calif., USA). Peptides of GLP-1 (7-36) amide, His-tagged GLP-1 (7-36), glucagon, and gastric inhibitory polypeptide (GIP) (SEQ ID NO: 12, full length, 153 amino acid residues; GIP 42 amino acid residues, SEQ ID NO: 13) were from LifeTein (Hillsborough, N.J., USA). Exendin 4 (Ex-4) and exendin 9 (Ex-9) were synthesized by Genomics BioSci & Technology (Taipei, Taiwan). The membrane-permeable cAMP 8-Br-2'-O-Me-cAMP-AM was from Axxora (Farmingdale, N.Y., USA). Adenylyl cyclase inhibitor MDL-12,330A hydrochloride, puromycin, G418, and 2-OG were from Sigma-Aldrich (St. Louis, Mo., USA). OEA, oleic acid (OA), and all other fatty acids and lipids were from Cayman (Ann Arbor, Mich., USA). RPMI-1640 tissue culture medium, minimum essential medium (MEM), FBS, sodium pyruvate, L-glutamine, HEPES, penicillin-streptomycin, amphotericin B, gentamicin, phenol red-free MEM, and 0.05% trypsin-EDTA were from Life Technologies (Carlsbad, Calif., USA). Coelentarazine 400a (DeepBlueC) was from Gold Biotechnology (St. Louis, Mo., USA). Phenylmethylsulfonyl fluoride (PMSF) was from USB (Cleveland, Ohio, USA). Oleoyl [9,10-$^3$H]ethanolamide ($^3$H-OEA) was from American Radiolabeled Chemicals Inc. (St. Louis, Mo., USA). [$^{125}$I]-Tyr-GLP-1(7-36) ($^{125}$I-GLP-1 (7-36)), UniFilter-96, GF/C and Microscint-20, -40 and The 96-well plates for scanning bioluminescent signals were from PerkinElmer (Boston, Mass., USA). Copper-nitrilotriacetate resin was from Jena Bioscience (Loebstedter Strase, Germany).

1.2 Construction of RG-cAMP Sensor—

Figure 1B:
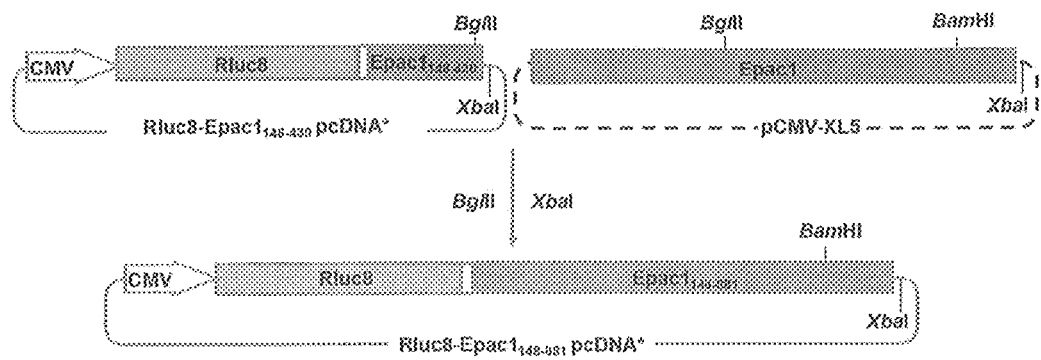
Figure 1C:
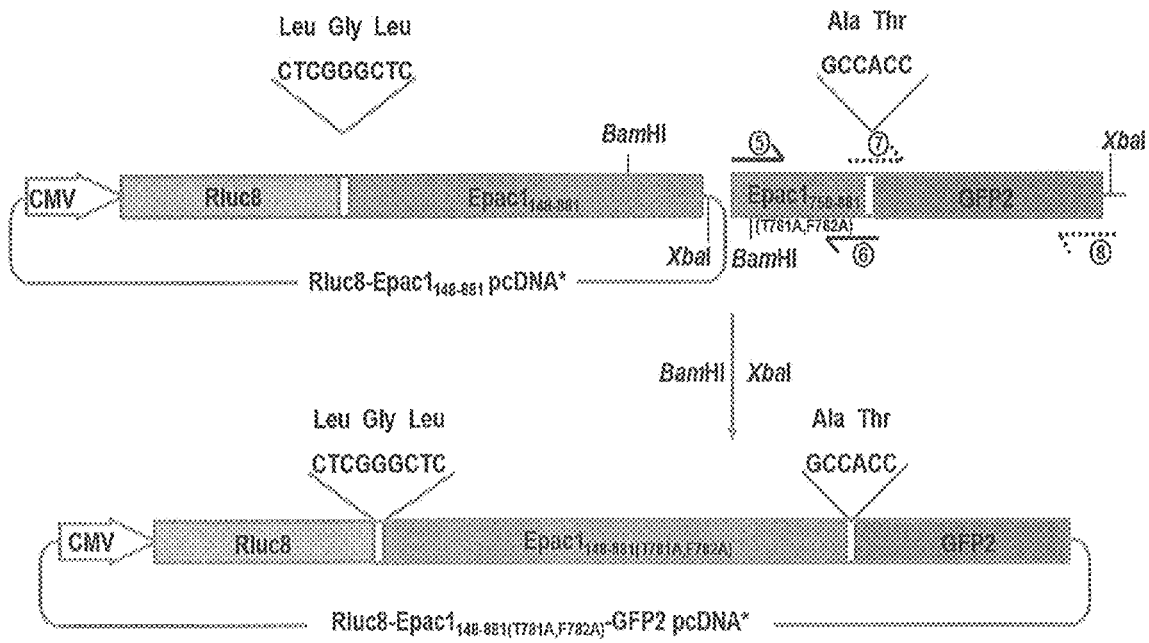

We replaced the energy donor and acceptor of the previously described Epac1 biosensor (22,23) with Rluc8 and GFP2, respectively, for enhanced bioluminescence resonance energy transfer (BRET)2 (24). Construction of expression vector for fusion protein RG-cAMP sensor is described in FIG. 1. Briefly, overlap extension PCR using Rluc8-pcDNA and pCMV-XL5-Epac1 as templates was used to generate Rluc8-Epac1$_{148-430}$pcDNA*, encoding Epac1 amino acids 148-430 (FIG. 1A). The fragment of pCMV-XL5-Epac1 encoding the C-terminal portion of Epac1 was then inserted into Rluc8-Epac1$_{148-430}$pcDNA* to yield construct Rluc8-Epac1$_{148-881}$pcDNA* (FIG. 1B). Epac1$_{750-881(T781A,F782A)}$, encoding Epac1 amino acids 148-881, where Thr781 and Phe782 have been changed to alanine, and GFP2 sequence were independently generated by PCR. Overlap extension PCR was used to generate the Epac1$_{750-881(T781A,F782A)}$-GFP2 fusion gene, followed by generation of the expression construct Rluc8-Epac1$_{148-881}$ $_{(T781A,F782A)}$-GFP2-pcDNA which codes for the fusion protein Rluc8-Epac1$_{148-881(T781A,F782A)}$-GFP2 (RG-cAMP sensor) (FIG. 1C).

1.3 Cell Culture and Transfection of Cell Lines—

The RINm5F cell line is derived from a rat islet-cell tumor (25,26) and expresses receptors for GLP-1, GIP and glucagon (27,28). RINm5F cells were seeded at a density of 3×10$^5$ cells/well in 24-well plates and cultured at 37° C. and 5% CO$_2$ in complete RPMI-1640 medium supplemented with 10% (v/v) FBS, 1 mM sodium pyruvate, 14 mM glucose, 1:1000 penicillin/streptomycin, 2 mM glutamine, and 35 mM sodium bicarbonate, pH 7.4, for 16 h. Before transfection, the medium was removed and replaced with 500 µL fresh complete RPMI-1640. Transfection was carried out using the Lipofectamine LTX Transfection Kit according to the manufacturer's protocol. Briefly, 0.5 µg plasmid RG-cAMP sensor in 0.1 ml Opti-MEM containing 1 µl Plus reagent and 3 µl LTX reagent was used to transfect the cells. Transfection complexes were added dropwise to the cells. After 12-h incubation, the medium containing the lipoplexes was removed and replaced with 500 µL complete RPMI-1640. The cultures were incubated for another 48 h; the population of green fluorescent cells was counted and transfection efficiency estimated. Cells from each well were transferred to a 15-cm culture dish with 20 ml complete RPMI-1640 containing 400 µg/ml G418 to select the stably transfected cells.

1.4 BRET (Bioluminescence Resonance Energy Transfer) and cAMP Response Assay—

RINm5F cells stably expressing the RG-cAMP sensor were seeded at 3×10$^4$ cells/well in 96-well white plates in 0.15 ml RPMI-1640 containing 400 µg/ml G418. On the next day, cells were washed twice with 0.1 ml phenol red-free MEM containing 5 mM HEPES and incubated in the same medium for 1 h. The medium was replaced with 90 µL of the same medium containing 1 mg/ml BSA and 5 µM Deep Blue C. The whole plate was immediately loaded onto a SpectraMax Paradigm Detection Platform equipped with a Dual-Color Luminescence Detection Cartridge and SoftMax Pro 6.2.2 (Molecular Devices, Sunnyale Calif., USA to obtain the background BRET signal based on the sequential integration of the luminescence detected at 370-450 nm and 500-530 nm over 60 to 150 s. Each well was then stimulated by adding 10 µl of 10× solutions of peptide and lipids and 1 mg/ml BSA in phenol red-free MEM containing 5 mM HEPES, and BRET signals were obtained immediately under identical settings. The BRET ratio is the ratio of light emitted between 90 and 300 s at 500-530 nm to that emitted at 370-450 nm. The cAMP response was expressed as a percentage of cAMP production and was calculated as 100×(BRET ratio from 0.01 nM GLP-1 (7-36) amide−BRET ratio from indicated concentration of peptide with or without lipids)/(BRET ratio from 0.01 nM GLP-1 (7-36) amide−BRET ratio from 250 nM GLP-1 (7-36) amide). The dose-response curve, maximal response, and concentration of peptide needed to yield half-maximal response (EC$_{50}$) were obtained by nonlinear regression to fit the data to the agonist vs. response equation using Prism software 5.0 (GraphPad, San Diego, Calif., USA). Unless specified, all cAMP response data are mean±SE are triplicate from three independent experiments with triplicate assays.

1.5 GLP-1 and OEA Binding Assay—

The putative GLP-1 peptide and lipid interaction were examined with a binding assay between tritium-labeled OEA ($^3$H-OEA) and His-tagged GLP-1 (7-36) peptide (FIG. 6A). $^3$H-OEA bound to His-tagged GLP-1 (7-36) peptide was separated from free $^3$H-OEA by incubating the binding reaction with copper-nitrilotriacetate resin ($Cu^{++}$-NTA) and subsequent centrifugation. $^3$H-OEA in the supernatant is the amount of free $^3$H-OEA. Specific bound $^3$H-OEA was obtained by subtracting the supernatant $^3$H-OEA of reaction from supernatant $^3$H-OEA of reaction without GLP-1. For binding of $^3$H-OEA to increasing amount of His-tagged GLP-1 (7-36), 0.2 uM of $^3$H-OEA and increasing concentration of His-tagged GLP-1 (7-36) peptide were mixed in 50 uL of Dulbecco's Phosphate Buffered Saline (DPBS) containing 0.02 mg/ml of bovine serum albumin (BSA) at RT for 90 min. Copper-nitrilotriacetate resin ($Cu^{++}$-NTA), 3 uL in 30 uL of DPBS, was added to capture all the His-tagged GLP-1 (up to 60 uM in 80 uL reaction), further incubated with rotation at RT for 30 min. The mixture was centrifuged at 4° C., 20600 g for 10 min to precipitate the His-tagged GLP-1 (7-36) trapped in resin, and 20 uL of supernatant containing the unbound free $^3$H-OEA was mixed with 120 uL of Microscint 40 (PerkinElmer Life and Analytical Sciences) for quantification of tritium by using single-photon counting (60 s/well read) on a TopCount scintillation counter (PerkinElmer Life and Analytical Sciences). Bound $^3$H-OEA=[supernatant $^3$H-OEA of binding reaction in the absence of His-tagged GLP-1 (7-36)]-[supernatant $^3$H-OEA of binding reaction with indicated amount of His-tagged GLP-1 (7-36)]. For the binding of 0.1 uM His-tagged GLP-1 (7-36) to increasing concentration of $^3$H-OEA, indicated concentration of $^3$H-OEA were incubated in the (total binding) presence or (nonspecific binding) absence of 0.1 uM of His-tagged GLP-1 (7-36), the free and bound $^3$H-OEA were separated as described above. Bound $^3$H-OEA=[supernatant $^3$H-OEA of nonspecific binding]-[supernatant $^3$H-OEA of total binding]. For competition assay to evaluate the binding of SEA and 2-OG to His-tagged GLP-1 (7-36), increasing concentration of 2-OG or SEA were incubated with 0.2 uM $^3$H-OEA in the (total binding) presence or (nonspecific binding) absence of 0.2 uM of His-tagged GLP-1 (7-36). The bound $^3$H-OEA and free $^3$H-OEA were separated as described above, and specific binding was calculated; Bound $^3$H-OEA=[supernatant $^3$H-OEA of nonspecific binding reaction]-[supernatant $^3$H-OEA in the total binding reaction]

1.6 Preparation of GLP-1 Receptor Membrane—

The pcDNA3 GLP-1R-V2R chimeric construct contains the first 440 amino acids of the GLP-1R (Met1 to Thr440) fused to the last 29 amino acids of the vasopressin V2 receptor (Ala343 to Ser371) (29) and separated by two alanine residues as linker. GLP-1R-V2R chimeric construct is inserted into the EcoRI site of pcDNA3 (pcDNA3-GLP-1R-V2R) such that expression of the chimeric protein is under the control of the CMV promoter. pcDNA3-GLP-1R-V2R was used to transfect U2OS osteosarcoma cells stably expressing β-arrestin2:GFP to obtain cell lines stably co-expressing GLP-1R-V2R and β-arrestin2:GFP. U2OS cells stably expressing GLP-1R-V2R were grown to 90% confluence (about $10^7$ cell per 15 cm dish). The medium were removed and washed twice with 30 ml Phosphate Buffered Saline (PBS), followed by adding 2.2 ml ice-cold homogenization buffer (20 mM HEPES, 1 mM EDTA, 0.7% protease inhibitor cocktail (Sigma-Aldrich, P8340) per dish. Scrape the cell immediately and centrifuge the scraped cell at 3000 g, 4° C. for 30 min. The pellet was resuspended with 5 ml homogenization buffer, then homogenized it with maximal speed of Polytron 3000 for 10 seconds on ice with 30 seconds interval rest, for 3 times. The homogenized cells were centrifuged for 10 min at 4° C. and 1000 g. Transfer the supernatant to fresh transparent centrifuge tube and centrifuge for 60 min at 4° C. and 55000 g. The pellets were resuspended with resuspension buffer (20 mM HEPES, 1 mM $MgCl_2$, 0.7% protease inhibitor) by passing through the 22 G needle 1 time, 25 G needle 3 times, then 26 G needle 1 time. The protein concentration of the membrane preparation was determined according to the instruction of Qubit Fluorometer (Life Technologies, Mass., USA). 4 to 5 ug of this membrane will yield greater than 5-fold signal:background with $^{125}$I-labeled GLP-1 at 5 nM in a 0.22 ml assay volume.

1.7 Receptor Binding Assay—

In 0.22 ml of 50 mM HEPES, pH 7.4, 5 mM $MgCl_2$, 1 mM $CaCl_2$ and 1 mg/ml BSA containing 3.9 ug of GLP-1 receptor membranes and varying concentration of $^{125}$I-GLP-1(7-36) radioactive ligand with or without 9.2 uM OEA and in the absence (total binding) or presence (nonspecific binding) of 500-fold excess unlabeled exendin 4. The reactions were incubated for 90 min. Prior to filtration, an FC 96-well harvest plate (Millipore. MAFC N0B 10) is coated with 0.5% polyethyleneimine for 30 min, then washed with 50 mM HEPES, pH 7.4. 0.1 ml of binding reaction is transferred to the filter plate, and washed 15 times (0.1 mL per well per wash) with ice cold 25 mM HEPES, pH 7.4 and 50 mM NaCl. The plate is dried followed by adding 30 uL of Microscint 20 (PerkinElmer, Waltham, Mass., USA) per well and the activity was determined by using single-photon counting (60 s/well read) on a TopCount scintillation counter (PerkinElmer Life and Analytical Sciences). Specific bindings were obtained by subtracting nonspecific binding from total binding. Dissociation constant ($K_d$) for GLP-1 (7-36) is obtained using Prism software 5.0 (Graph Pad). Data shown are the mean±standard error of the mean (SE) are duplicate from three independent experiments.

1.8 In Vitro Assay of Trypsin Activity in the Presence of OEA—

To determine whether OEA affects trypsin activity, we used the Trypsin Activity Colorimetric Test Kit (BioVision, Milpitas, Calif., USA). Briefly, 2 μL substrate was added to a well in 96-well plate containing 48 μL 0.000125% trypsin in the presence or absence of 92 uM OEA. Reactions were conducted at room temperature, and the extent of cleavage was monitored by real-time reading of optical density (OD) at 405 nm

1.9 Limited Trypsin Digestion of GLP-1 (7-36) Amide—

Trypsin digestion was carried out at 37° C. for 30 min in 0.1 ml phenol red-free MEM containing 5 mM HEPES, pH 7.0, 2 μM GLP-1 (7-36) amide, $2\times10^{-3}$% to $2.5\times10^{-5}$% of trypsin (prepared by diluting 0.05% trypsin-EDTA) and 92 to 1 μM of OEA. Reaction was terminated by incubation at 94° C. for 30 min and then at 4° C. for 10 min, followed by addition of PMSF to 1 mM.

1.10 Determination of Concentrations of GLP-1 (7-36) Amide and Glucagon and GIP Peptides—

Molar concentrations were determined using the equation whereby peptide concentration (M)=($OD_{280}$×fold dilution)/ (1200+5560); 1200 and 5560 are the molar extinction coefficients for tyrosine and tryptophan, respectively.

2. Results

2.1 Construction of RG-cAMP Sensor—

To reduce BRET background and obtain better separation of the donor and acceptor energy emission peaks, we replaced the energy donor and acceptor in the early version Epac1 cAMP biosensor (22,23) with Rluc8 (20) and GFP2, respectively, for use in enhanced BRET2 (24) (FIG. 1 A-C). Detailed description of generation of the expression construct for the RG-cAMP sensor is described in Experimental Procedures.

2.2 Validation of the RG-cAMP Sensor in RINm5F Cells—

Figure 2B:
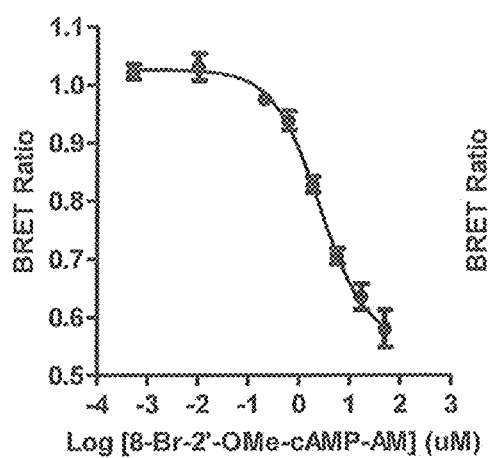
Figure 2C:
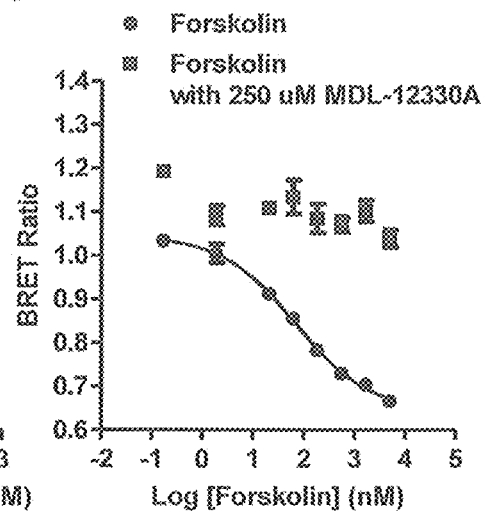
Figure 3A:
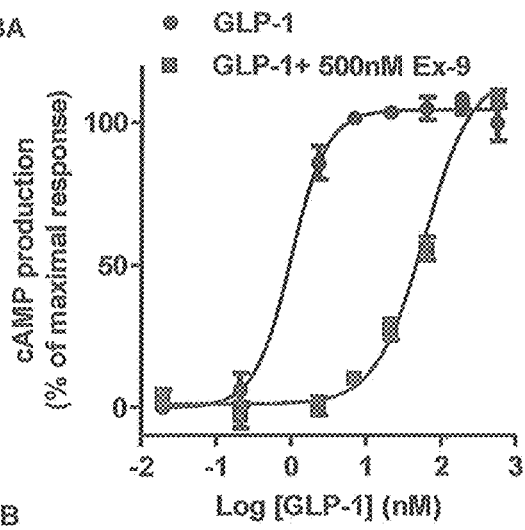
Figure 3B:
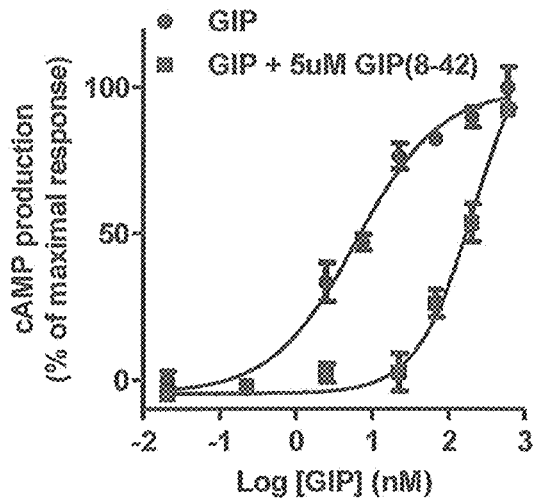
Figure 3C:
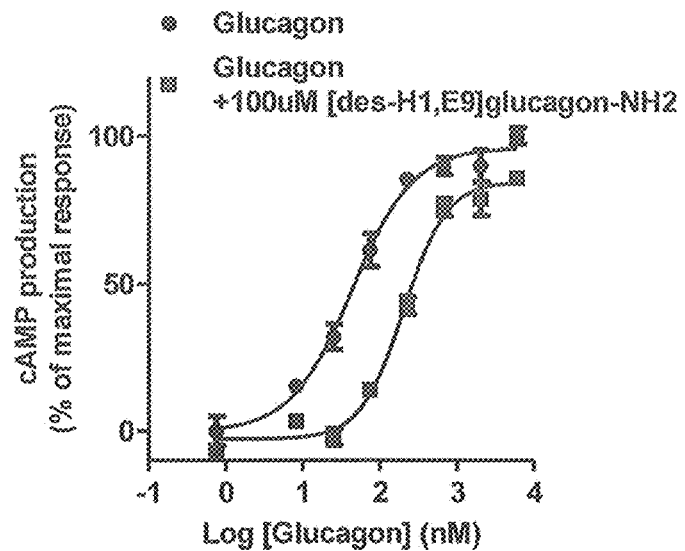

The use of the RG-cAMP sensor (FIG. 2A) as an intracellular cAMP biosensor in RINm5F cell line, which is derived from a rat islet-cell tumor, in the BRET assay was validated using the membrane-permeable cAMP analog 8-Br-2'-OMe-cAMP-AM, the adenylyl cyclase activator forskolin, and the adenylyl cyclase inhibitor MDL-12330A. As shown in FIG. 2B, increasing the level of cAMP analog resulted in reduction of the BRET ratio in a concentration-dependent and saturable manner. The BRET ratio started to decrease from 1.0 as the concentration of 8-Br-2-O-Me-cAMP-AM increased to 0.2 µM and stopped dropping at 0.55 when the concentration of 8-Br-2-O-Me-cAMP-AM reached 50 µM. The concentration of 8-Br-2-O-Me-cAMP-AM at which half maximal reduction of BRET ratio is elicited ($EC_{50}$) was determined to be 2.6 µM. This analysis shows that 0.45 unit of BRET ratio reduction corresponds to a concentration change of 8-Br-2-O-Me-cAMP-AM from 0.2 µM to 50 µM. This observation led us to further test whether this cAMP biosensor would respond to forskolin which activate adenylyl cyclase and leads to cAMP production. As shown in FIG. 2C, forskolin treatment resulted in reduction of BRET ratio in a dose-dependent and saturable manner; the BRET ratio started to decrease at a concentration of 1.8 nM forskolin, and reduction became saturated as forskolin concentration reached 5000 nM. The forskolin-elicited BRET response was eliminated in the presence of 250 µM MDL-12,330A, a potent adenylyl cyclase inhibitor. The change in basal cAMP level to that maximally stimulated by forskolin corresponds to a BRET ratio reduction of 0.3 unit. The $EC_{50}$ for forskolin was determined to be 70 nM. This observation demonstrated that activation of adenylyl cyclase leads to increased intracellular cAMP. MDL-12,330A which in turn inhibits the enzyme, abolished the activating effect of forskolin. Both processes can be sensed by the RG-cAMP sensor in the cells. RINm5F cells endogenously express Gαs-coupled receptors for GLP-1, GIP, and glucagon (27,28). cAMP production in RINm5F cells expressing the RG-cAMP sensor showed dose-dependent and saturable responses to GLP-1 (7-36) amide, GIP, and glucagon (FIG. 3 A-C). These responses were curtailed by the corresponding antagonists, Ex-9, GIP(8-42) (SEQ ID NO: 14) (30), and [des-His1,Glu9]-glucagon amide (31), respectively, indicating that the cAMP responses were mediated by specific activation of the cognate receptors (FIG. 3 A-C). The $EC_{50}$ was 1.3, 6, and 43 nM for GLP-1 (7-36) amide, GIP, and glucagon, respectively. These results validated the applicability of RG-cAMP sensor in detecting intracellular cAMP level in response to incretin and glucagon stimulation in RINm5F cells.

2.3 OEA and 2-OG Potentiate cAMP Production in Response to GLP-1 (7-36) Amide—

Figure 4A:
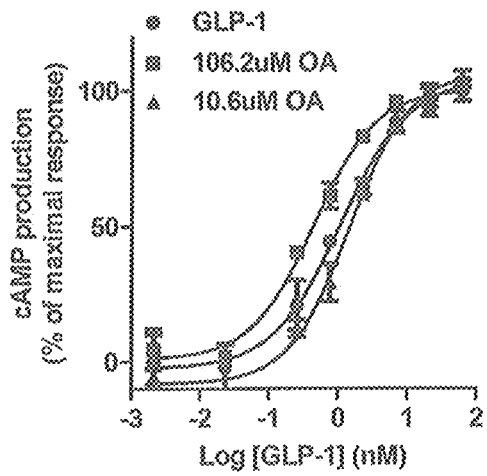
FIG. 4A-4E shows the effect of oleic acid (OA), linoleic acid (LA), stearic acid (SA), α-linolenic acid (ALA), γ-linolenic acid (γ-LA), stearoyl ethanolamide (SEA), palmitoyl ethanolamide (PEA) and n-oleoyl dopamine (ODA) on cAMP response to the titration of GLP-1 (7-36) amide in RINm5F cells. cAMP production in response to the titration of GLP-1 (7-36) amide.
Figure 4B:
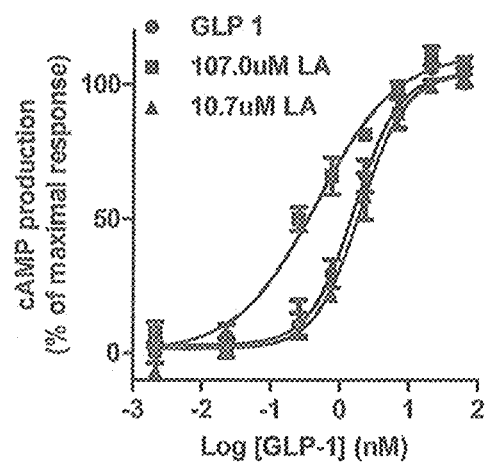
Figure 4C:
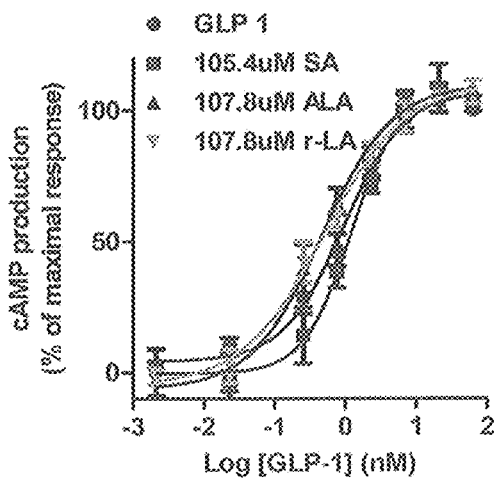
Figure 4D:
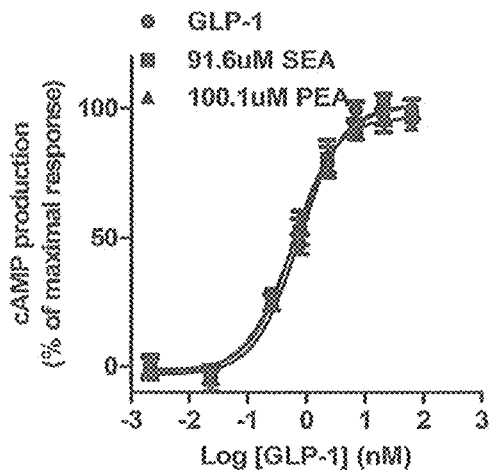
Figure 4E:
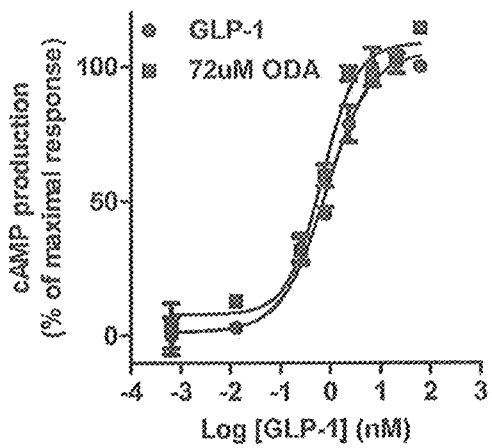

In a preliminary test of the ability of the 18-carbon fatty acids and their lipid derivatives to enhance the GLP-1R cAMP response using BRET assay, oleic acid (OA; 18:1) and linoleic acid (LA; 18:2) at 106 and 107 uM, respectively, consistently but mildly left-shifted the dose response curve of GLP-1 (7-36) amide (FIGS. 4 A and B), whereas stearic acid (SA), α-linolenic acid (ALA) and γ-linolenic acid (γ-LA) did not show such an effect (FIG. 4C). Other lipids tested that did not affect GLP-1 potency in receptor signaling included stearoylethanolamide (SEA), palmitoylethanolamide (PEA), and n-oleoyldopamine (ODA) (FIG. 4 D-E). We then examined endogenous lipid derivatives containing OA as their acyl-lipid backbone. OEA and 2-OG, at a concentration of 9 to 8 uM markedly left-shifted the dose-response curve for GLP-1 (7-36) amide to stimulate cAMP production in RINm5 F cells (FIGS. 5 A and B). Responses were enhanced when the concentration of GLP-1 reach 20 pM, the $EC_{50}$ of GLP-1 (7-36) amide was reduced from 1.29 nM to 0.12 and 0.11 nM by 9.2 uM OEA and 8.4 uM 2-OG, respectively (Table 1A and 2B).

TABLE 1

(A)

Influence of OEA on $EC_{50}$ (nM) of GLP-1 (7-36) amide

| Lipids | Lipid concentration (uM) | | | |
|---|---|---|---|---|
| | 0 | 9.2 | 3.1 | 1 |
| OEA | 1.29 ± 0.36 | — | 0.12 ± 0.02 | 0.44 ± 0.12 | 1.03 ± 0.35 |

Influence of 2-OG on $EC_{50}$ (nM) of GLP-1 (7-36) amide

| Lipids | Lipid concentration (uM) | | | |
|---|---|---|---|---|
| | 0 | 8.4 | 2.8 | 0.9 |
| 2-OG | 1.29 ± 0.36 | — | 0.11 ± 0.04 | 0.26 ± 0.09 | 0.94 ± 0.39 |

The enhancement is dependent on the GLP-1 (7-36) amide, as the effect diminished when the concentration of GLP-1 (7-36) reduced to 2 µM. To examine if this enhancement is specific for GLP-1 (7-36) amide, we further examined if OEA and 2-OG could enhance the potency of exendin 4 (Ex-4), an analog of mammalian GLP-1. Ex-4 dose-dependently stimulated cAMP production and reached saturation at a concentration of 10 nM, with an $EC_{50}$ of 0.5±0.13 nM (FIGS. 5 C and D); however, the potency of Ex-4 was unaltered by the addition of OEA or 2-OG to a concentration up to 27 uM (FIGS. 5 C and D). Therefore, OEA and 2-OG do not enhance the Ex-4-stimulated cAMP response in RINm5F cells. RINm5F cell is a rat insulinoma cell line, should expresses many receptors involved in cAMP production other than GLP-1R. In order to investigate if receptors other than GLP-1 receptor participate in OEA or 2-OG mediated enhancement of cAMP production by GLP-1, we examined if this enhancement and cAMP responses still occur when GLP-1 receptors signaling were blocked by its antagonist exendin 9. As shown in FIG. 5E, 9 uM OEA or 8.4 uM 2-OG remarkably enhanced the cAMP responses to 200 µM of GLP-1 (7-36) amide in RINm5F cells. This enhancement and cAMP responses were barely detectable when GLP-1 receptor signaling was blocked by the presence of 500 nM exendin 9. This analysis clearly illustrated that most of OEA or 2-OG mediated enhancement of cAMP response by GLP-1 is through GLP-1 receptors. This analysis revealed specificity of these lipids in enhancing GLP-1 (7-36) amide potency, and not that of other structurally-related peptides or receptors other than GLP-1R.

2.4 GLP-1 Specifically Binds to OEA and 2-OG—

As both OEA and 2-OG enhance the potency of GLP-1 (7-36) but not that of exendin 4, one possible explanation is that these lipids may interact specifically with GLP-1 (7-36) amide. We further looked into the binding between His-tagged GLP-1 (7-36) (FIG. 6A) and $^3$H-OEA. His-tagged GLP-1 (7-36) displays comparable response to OEA and to stimulate cAMP response as GLP-1 (7-36) amide does. In a binding reaction, the peptide bound-$^3$H-OEA together with the free peptide were captured by $Cu^{++}$-NTA resin and separated from free $^3$H-OEA after centrifugation. 3 ul of $Cu^{++}$-NTA resin in 80 ul binding reaction volume has been validated to be sufficient to capture all the His-tagged GLP-1 (7-36) when the highest concentration of His-tagged GLP-1(7-36) used in the assay. FIG. 6B shows the binding of 0.2 uM $^3$H-OEA was increased with increasing concentration of His-tagged GLP-1 (7-36), indicating that His-tagged GLP-1 (7-36) binds to $^3$H-OEA in a dose dependent and saturable way; the estimated concentration of GLP-1 to achieve half-maximal binding of OEA is 0.16±0.05 uM. FIG. 6C showed an increased binding of $^3$H-OEA to 0.1 uM of His-tagged GLP-1 (7-36) with increasing concentration of $^3$H-OEA, also indicating that $^3$H-OEA binds to His-tagged GLP-1 (7-36) in a dose dependent way, and the concentration of $^3$H-OEA to achieve half-maximal bind is estimated to be 0.28±0.07 uM. As the potency of GLP-1 to stimulate cAMP production is enhanced by OEA and 2-OG but not by SEA, we also analyzed binding of 2-OG and SEA to His-tagged GLP-1 (7-36) in a competition assay. As shown in FIG. 6D, the His-tagged GLP-1(7-36) bound $^3$H-OEA decreased as the concentration of 2-OG increased from 0.125 uM to 2.0 uM and the Ki is estimated to be 0.1±0.03 uM. SEA, on the other hand, did not affect the binding of $^3$H-OEA to His-tagged GLP-1(7-36). These observations indicate that OEA and 2-OG specifically bind to His-tagged GLP-1 (7-36).

2.5 Effect of OEA on Saturation Binding of GLP-1 to GLP-1 Receptor—

Figure 7A:
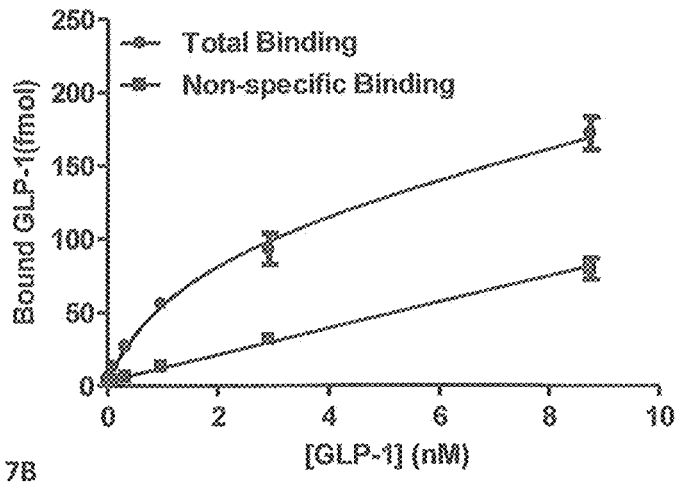
FIG. 7A-7C shows the effect of OEA on saturation binding for GLP-1R. (●) Total and (■)non-specific binding of $^{125}$I-GLP-1(7-36) to GLP-1R-V2R membrane in the (FIG. 7A) absence or (FIG. 7B) presence of 9.2 uM of OEA.
Figure 7B:
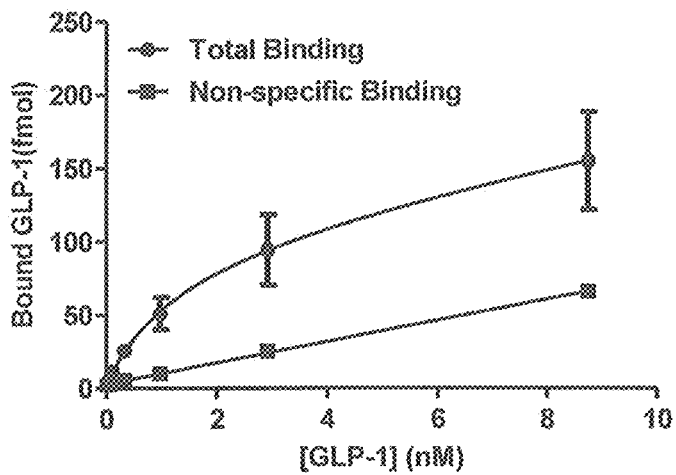
Figure 7C:
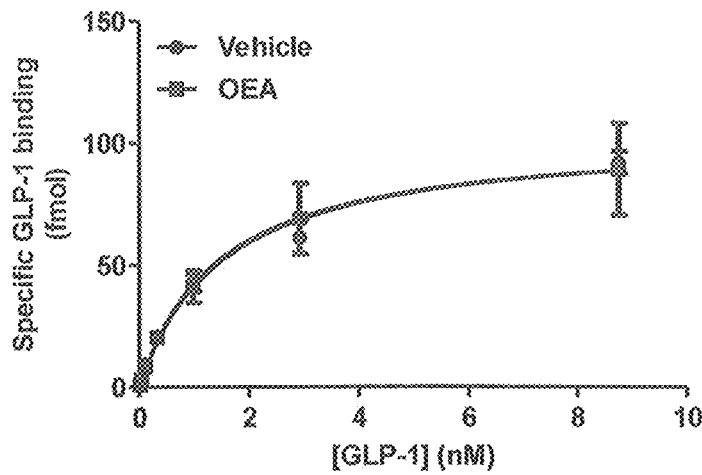

As OEA binds to and enhances the potency of GLP-1 (7-36), we further investigated if this effect may result from an enhanced binding affinity of GLP-1 (7-36) to GLP-1 receptor. We perform saturation binding assay to examine effect of OEA on GLP-1 receptor binding affinity. As shown in FIG. 7A, binding of $^{125}$I-GLP-1 to GLP-1 receptor membrane is dose dependent and saturable, the dissociation constant Kd and the maximal binding (Bmax) were measured to be 1.5±0.25 nM and 51±2.9 pmole/mg of membrane, respectively. The saturation binding curve was barely affected by 9.2 uM OEA which maximally enhances the potency of cAMP production by GLP-1 (FIG. 7B). The Kd and Bmax measured in the presence of 9.2 uM OEA was 1.4±0.5 nM and 51±6.5 pmole/mg of membrane, respectively. Specific binding of $^{125}$I-GLP-1 (7-36) to GLP-1 receptor in the presence or absence of 9.2 uM of OEA are almost superimposed (FIG. 7C). This analysis revealed that GLP-1's affinity and capacity to bind GLP-1 receptor are comparable in the presence or absence of OEA. It is concluded that 9.2 uM OEA, though maximally enhances the potency of GLP-1 (7-36) to stimulate cAMP response, does not affect the physical affinity between GLP-1 and its cognate receptor.

2.6 Effect of OEA on Trypsin Inactivation of GLP-1 (7-36) Amide—

Figure 8A:
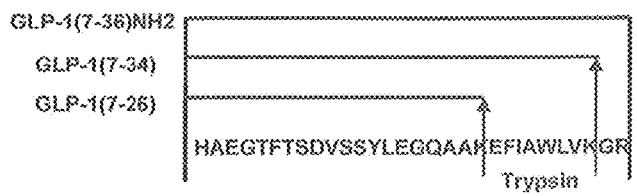
FIG. 8A-8F shows the effect of OEA on trypsin inactivation of GLP-1(7-36) amide.
Figure 8B:
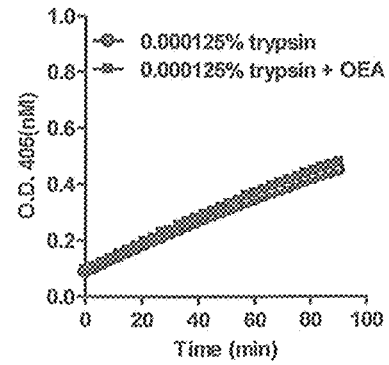
Figure 8C:
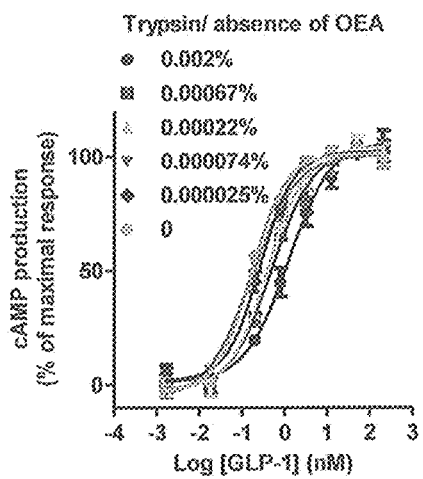
Figure 8D:
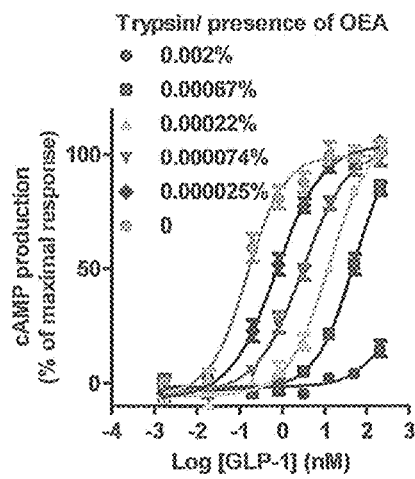
Figure 8E:
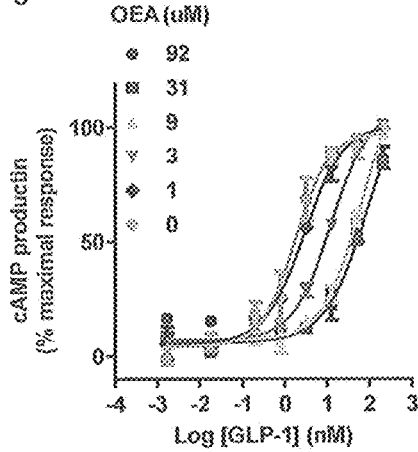
Figure 8F:
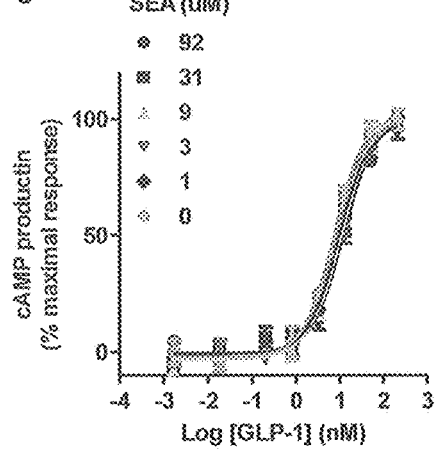

OEA specifically binds to GLP-1 (7-36) amide and enhances GLP-1 to stimulate cAMP production while not affects the receptor binding affinity, suggestive of a potential lipid induced structural change of GLP-1 peptide. We probed the potential conformation of GLP-1 (7-36) amide based on its susceptibility to trypsin digestion. The two trypsin cleavage products of GLP-1 (7-36) amide are an inactive GLP-1(7-26) and a partially active GLP-1(7-34) (FIG. 8A) (32). We carried out limited trypsin digestion to determine whether the putative lipid-peptide interaction may alter the susceptibility of GLP-1 (7-36) amide to trypsin and result in a change in activity measured by cAMP responses. Residual activity in stimulating cAMP production after trypsin treatment was used to examine susceptibility of the peptide to trypsin digestion. SEA and OEA were tested as representative non-signal-enhancing and signal-enhancing lipids, respectively. To obtain a workable concentration of trypsin for the limited digestion of 2 uM GLP-1 (7-36) amide, we titrated trypsin concentration from $2.5 \times 10^5$% to 0.002% vs GLP-1 (7-36) amide activity to stimulate cAMP production in RINm5F cells. As shown in FIG. 8C, the residual activity of GLP-1 (7-36) to stimulate cAMP production was gradually reduced as trypsin concentration increased from $2.5 \times 10^{-5}$% to 0.002%. The activity was decreased by a factor of 10 when GLP-1 (7-36) was digested with 0.002% of trypsin. This analysis demonstrated that trypsin inactivates GLP-1 (7-36) amide in a dose-dependent manner. When the trypsin cleavage reactions were carried out in the presence of 92 uM OEA (FIG. 8D), GLP-1 activity was dramatically reduced by a factor of more than 300 (FIG. 8D). This analysis revealed that OEA remarkably facilitated GLP-1 (7-36) to trypsin digestion. This is not due to an activation of trypsin by OEA, as OEA does not affect the innate trypsin activity (FIG. 8B). To analyze whether the effect of OEA on trypsin inactivation of GLP-1 was dependent on the concentration of OEA, digestion of GLP-1 (7-36) amide with 0.00067% trypsin was carried out with increasing concentrations of OEA. FIG. 8E shows that as the concentration of OEA increased from 1 uM to 92 uM, the residual activity of GLP-1 (7-36) amide after trypsin digestion was reduced by a factor of more than 40. The effect of OEA became saturated as it reached a concentration of 9 uM. These analyses revealed that OEA dose-dependently and saturably promotes GLP-1 (7-36) peptide to trypsin cleavage. In contrast, SEA at concentrations ranging from 1 uM to 92 uM did not affect trypsin digestion of GLP-1 (7-36) amide (FIG. 8F). Our findings clearly revealed that trypsin digestion of GLP-1 (7-36) amide was facilitated by OEA. This is not due to the activation of trypsin by OEA, as OEA did not affect the innate enzymatic activity of trypsin (FIG. 8B). Taken together, these data show that the susceptibility of GLP-1 peptide to trypsin cleavage is specifically increased by OEA, most likely due to a conformational change in GLP-1 (7-36) amide.

3. Discussion

The real time intracellular cAMP assay used in our study is an enhanced BRET2 (24) assay that has better separation of the energy emitted by the donor and acceptor (22,33) and yields data comparable to that obtained by other previously reported methods (22,33). This enhanced assay has the advantage of being able to monitor intracellular cAMP production (not cAMP accumulation) in the absence of phosphodiesterase inhibition (e.g., by 3-isobutyl-1-methyl-xanthine [IBMX]), as well as being a higher-throughput assay, based on use of 96- or 384-well plates.

In addition, OEA, and 2-OG are both endogenous fatty acids reported to be ligands for GPCR (GPR119) but, when present alone in our assay did not elicit cAMP responses even with concentrations as high as 10 times (33 M for OEA and 28 μM for 2-OG) the reported $EC_{50}$ (2.9 μM) for these lipids to activate GPR119 (34). These data agree with the observation that the RINm5F cell line is devoid of GPR119 receptor signaling (35,36), and the assay is thus free from the interference of GPR119 signaling.

In the present communication we present evidence that specific endocannabinoid-like lipids (OEA and 2-OG) increase the potency of GLP-1 to stimulate cAMP production, while SEA showed little effect. Lipid modification of glucagon has been reported to alter receptor selectivity between GLP-1R and GCGR. It is also possible that binding of OEA or 2-OG to GLP-1 peptide may activate receptors other than GLP-1R in RINm5F cells and results in enhanced cAMP production. The present studies show that the enhancement effect of OEA or 2-OG and cAMP response was barely detected when GLP-1 Rs in RINm5F cells were blocked by 500 nM of GLP-1R antagonist (FIG. 5E). This observation indicated that lipid enhancement and cAMP response is mostly likely mediated by GLP-1R. The result also shows that receptor other than GLP-1R in RINm5F cells play little role in potency enhancement by OEA or 2-OG. Several mechanisms may account for this phenomenon. At least three possible mechanisms depend on GLP-1R signaling. The receptor, it may interact with lipids, could enhance its coupling to Gαs upon ligand binding. Alternatively, the GLP-1 peptide, it may also interacts with lipids, could enhance its potency to stimulate the coupling of GLP-1R to Gαs. Or both of the mechanisms mentioned above account for the observation. Several lines of evidences imply that endocannabinoid-like lipids interact with GLP-1 (7-36) peptide. First, we are not able to observe detectable specific binding of $^3$H-OEA to GLP-1 receptor. Secondly both OEA and 2-OG selectively enhance the potency of the GLP-1 (7-36) amide, but not that of Ex-4, indicating interaction with selective peptide. Thirdly, that a signal-enhancing lipid, OEA, but not the non-signal-enhancing lipid SEA, facilitates trypsin inactivation of the peptide, also suggested a lipid-peptide interaction. Finally, GLP-1 (7-36) binds to OEA and 2-OG but not to SEA revealed a specific binding of OEA or 2-OG to GLP-1(7-36) peptide. Thus the available experimental data are in line with a simple model that specific endocannabinoid-like lipids can bind to GLP-1 and form a complex with enhanced potency to stimulate cAMP response. Surprisingly, interacting of OEA with GLP-1 does not affect the binding affinity to GLP-1 receptor, the lipid-peptide interactions are mostly dedicated to enhancing the potency to stimulate the coupling of GLP-1 receptor to cAMP production. It is not unusual that receptor binding energy of GLP-1 single point mutants may or may not be realized to its signaling potency (37). OEA but not SEA facilitates susceptibility of GLP-1 to trypsin cleavage, is consistent with the specific binding of OEA not SEA to GLP-1. Putting these findings together, it is most likely that binding of OEA to GLP-1 may induce a conformational change of the peptide and is accompanied with an enhancement in potency. This proposed model is evocative of the scenario in which peptide ligands for class B GPCRs can be induced to undergo a conformational change in the presence of lipids (38) or upon interaction with their cognate receptors (39).

Apart from the well-known effects of postprandial GLP-1 secretion on pancreatic β cells for glycemic control, our knowledge of how GLP-1Rs broadly expressed in tissues serving different functions can be differentially regulated is far from complete (for review see (4)). By changing the potency, our results present a novel way to regulate GLP-1 receptor signaling without altering the extracellular level of GLP-1 peptide. GLP-1Rs in the brain stem are considered activated by the centrally-derived GLP-1, which is transmitted through neural fibers in most of brain areas (11,12, 40). However, neurons expressing GLP-1Rs in notable areas, such as caudal hippocampus and the dopaminergic neurons in the substantia nigra, have no apparent innervations from GLP-1-producing neurons (1,3,14). Both areas are anatomic sites of deficient functions in disease that are ameliorable by GLP-1 analog therapy, which improves memory/learning in an Alzheimer mouse model and Parkinson symptoms in humans (5,6,41). It has been suggested that GLP-1Rs in these areas might be activated by the circulating GLP-1 in cerebrospinal fluid and blood (40), which is normally at a level that is probably below the threshold concentration for GLP-1R activation (42). Given that a 2- to 5-fold postprandial surge in plasma GLP-1 level can activate pancreatic 13 cells to release insulin, induction of a 10-fold enhancement in potency by lipids may be sufficient to allow the basal level of GLP-1 to activate its receptors.

The lipids OEA and 2-OG are described as endocannabinoid-like because they share structural homology with the endocannabinoids, but do not activate the cannabinoid receptors. Our knowledge of the biology of these endocannabinoid-like lipids is sketchy, as they have attracted research interest only in recent years, because each is known to activate other receptors, including GPR119 and peroxisome proliferator-activated receptor (for review see (43)). In general, endocannabinoid-like lipids are present in variable amounts in different tissues (44). Their levels are also subject to change following chronic feeding of a diet rich in select types of oil (e.g., olive oil predominantly yields OEA and 2-OG (43)). As the levels of OEA and 2-OG are much higher (19,45,46), these endocannabinoid-like lipids would seem similarly well situated as signal modulators in the brain. OEA is generated in tissues in a stimulus-dependent manner and is quickly removed by enzymatic hydrolysis, indicating a function in signaling (for review see (17)). The concentration of 2-OG is significantly elevated in the blood of hibernating animals compared to that of active animals (18). The level of 2-OG is in the range of 2-3 nmol/g of whole brain tissues, but in specific regions of the brain can go up to 100 nmol/g of tissue and is also subject to physiological regulation (19). Distinct from the mode of all lipid mediators that activate receptors in their own right, these endocannabinoid-like lipids regulate GLP-1R signaling by enhancing the potency of GLP-1. In conclusion, local tissue levels of these lipids are varied and regulated physiologically; thus, they can modulate the potency of GLP-1 in a tissue- and physiology-dependent manner. This will allow temporal and spatial regulation of GLP-1R signaling without changing basal level of GLP-1.

Finally, deterioration in GLP-1 signaling response in type 2 diabetes, rather than reduced GLP-1 secretion is associated with the pathogenesis of the disease (47). Such patients have impaired incretin effect, despite normal GLP-1 secretion (48) and normal GLP-1 secretion in response to oral glucose or meal tests (47). Clinically, the administration of GLP-1 analog has been successful in ameliorating reduced GLP-1 signaling in type 2 diabetes; likewise, similar therapeutic effects may be achieved with positive modulators for GLP-1 peptide, which may restore the function of GLP-1 signaling that is more in line with physiological demands. Because cAMP is sufficient for glucose-dependent insulin release (49), one could investigate whether compounds capable of enhancing the cAMP response to GLP-1 (7-36) amide stimulation in RINm5F cells may represent a new class of therapeutic agents, or in the form of nutrient derivatives, to treat or prevent type 2 diabetes and other GLP-1 signaling-related diseases.

In summary, we develop a new biosensor for detecting intracellular cAMP, which is more sensitivity and workable in high-throughput assays, as compared to conventional technology. In addition, by using our biosensor technology, some specific endogenous lipids to modulate the potency of a GLP-1 ligand are found, which in turn are subjected to temporal and spatial regulation. This novel mode of regulation allows GLP-1Rs signaling in different tissues to be differentially activated without changing the basal level of GLP-1. This mode of regulation is distinct from the traditional model, which requires that the extracellular levels of ligand are the primary factors contributing to regulation of GPCR signaling. Our results show that the potency of the ligand itself can be a target for modulation. These findings could further lead to exploration of a distinct class of endogenous modulators and represent novel targets for drug discovery.

REFERENCES

1. Hamilton, A., and Holscher, C. (2009) Receptors for the incretin glucagon-like peptide-1 are expressed on neurons in the central nervous system. *Neuroreport* 20, 1161-1166
2. Lockie, S. H. (2013) Glucagon-like peptide-1 receptor in the brain: role in neuroendocrine control of energy metabolism and treatment target for obesity. *J. Neuroendocrinol.* 25, 597-604
3. Merchenthaler, I., Lane, M., and Shughrue, P. (1999) Distribution of pre-pro-glucagon and glucagon-like peptide-1 receptor messenger RNAs in the rat central nervous system. *J. Comp. Neurol.* 403, 261-280
4. Campbell, J. E., and Drucker, D. J. (2013) Pharmacology, physiology, and mechanisms of incretin hormone action. *Cell Metab* 17, 819-837
5. Aviles-Olmos, I., Dickson, J., Kefalopoulou, Z., Djamshidian, A., Kahan, J., Fmedsci, P. E., Whitton, P., Wyse, R., Isaacs, T., Lees, A., Limousin, P., and Foltynie, T. (2014) Motor and Cognitive Advantages Persist 12 Months After Exenatide Exposure in Parkinson's Disease. *J. Parkinsons Dis.* 4(3), 337-344.
6. Holscher, C. (2014) Central effects of GLP-1: new opportunities for treatments of neurodegenerative diseases. *J. Endocrinol.* 221, T31-41
7. Lonborg, J., Kelbaek, H., Vejlstrup, N., Botker, H. E., Kim, W. Y., Holmvang, L., Jorgensen, E., Helqvist, S., Saunamaki, K., Terkelsen, C. J., Schoos, M. M., Kober, L., Clemmensen, P., Treiman, M., and Engstrom, T. (2012) Exenatide reduces final infarct size in patients with ST-segment-elevation myocardial infarction and short-duration of ischemia. *Circ. Cardiovasc. Interv.* 5, 288-295
8. Orskov, C. (1992) Glucagon-like peptide-1, a new hormone of the entero-insular axis. *Diabetologia* 35, 701-711
9. Nadkarni, P., Chepurny, O. G., and Holz, G. G. (2014) Regulation of Glucose Homeostasis by GLP-1. *Prog. Mol. Biol. Transl. Sci.* 121, 23-65
10. Meier, J. J., Nauck, M. A., Kranz, D., Holst, J. J., Deacon, C. F., Gaeckler, D., Schmidt, W. E., and Gallwitz, B. (2004) Secretion, Degradation, and Elimination of Glucagon-Like Peptide 1 and Gastric Inhibitory Polypeptide in Patients with Chronic Renal Insufficiency and Healthy Control Subjects. *Diabetes* 53, 654-662
11. Gu, G., Roland, B., Tomaselli, K., Dolman, C. S., Lowe, C., and Heilig, J. S. (2013) Glucagon-like peptide-1 in the rat brain: distribution of expression and functional implication. *J. Comp. Neurol.* 521, 2235-2261
12. Larsen, P. J., Tang-Christensen, M., Holst, J. J., and Orskov, C. (1997) Distribution of glucagon-like peptide-1 and other preproglucagon-derived peptides in the rat hypothalamus and brainstem. *Neuroscience* 77, 257-270
13. Llewellyn-Smith, I. J., Gnanamanickam, G. J., Reimann, F., Gribble, F. M., and Trapp, S. (2013) Preproglucagon (PPG) neurons innervate neurochemically identified autonomic neurons in the mouse brainstem. *Neuroscience* 229, 130-143
14. Llewellyn-Smith, I. J., Reimann, F., Gribble, F. M., and Trapp, S. (2011) Preproglucagon neurons project widely to autonomic control areas in the mouse brain. *Neuroscience* 180, 111-121
15. Widmann, C., Burki, E., Dolci, W., and Thorens, B. (1994) Signal transduction by the cloned glucagon-like peptide-1 receptor: comparison with signaling by the endogenous receptors of beta cell lines. *Mol. Pharmacol.* 45, 1029-1035
16. Mayo, K. E., Miller, L. J., Bataille, D., Dalle, S., Goke, B., Thorens, B., and Drucker, D. J. (2003) International Union of Pharmacology. XXXV. The glucagon receptor family. *Pharmacol. Rev.* 55, 167-194
17. Ezzili, C., Otrubova, K., and Boger, D. L. (2010) Fatty acid amide signaling molecules. *Bioorg. Med Chem. Lett.* 20, 5959-5968
18. Vaughn, L. K., Denning, G., Stuhr, K. L., de Wit, H., Hill, M. N., and Hillard, C. J. (2010) Endocannabinoid signalling: has it got rhythm? *Br. J. Pharmacol.* 160, 530-543
19. Roberts, C. J., Stuhr, K. L., and Hillard, C. J. (2012) Swim stress differentially affects limbic contents of 2-arachidonoylglycerol and 2-oleoylglycerol. *Neuroscience* 204, 74-82
20. Loening, A. M., Fenn, T. D., Wu, A. M., and Gambhir, S. S. (2006) Consensus guided mutagenesis of *Renilla* luciferase yields enhanced stability and light output. *Protein Eng. Des. Sel.* 19, 391-400
21. Hsu, Y. Y., Liu, Y. N., Lu, W. W., and Kung, S. H. (2009) Visualizing and quantifying the differential cleavages of the eukaryotic translation initiation factors eIF4GI and eIF4GII in the enterovirus-infected cell. *Biotechnol. Bioeng.* 104, 1142-1152
22. Jiang, L. I., Collins, J., Davis, R., Lin, K. M., DeCamp, D., Roach, T., Hsueh, R., Rebres, R. A., Ross, E. M., Taussig, R., Fraser, I., and Sternweis, P. C. (2007) Use of a cAMP BRET sensor to characterize a novel regulation of cAMP by the sphingosine 1-phosphate/G13 pathway. *J. Biol. Chem.* 282, 10576-10584
23. Barak, L. S., Salahpour, A., Zhang, X., Masri, B., Sotnikova, T. D., Ramsey, A. J., Violin, J. D., Lefkowitz, R. J., Caron, M. G., and Gainetdinov, R. R. (2008) Pharmacological characterization of membrane-expressed human trace amine-associated receptor 1 (TAAR1) by a bioluminescence resonance energy transfer cAMP biosensor. *Mol. Pharmacol.* 74, 585-594
24. Bacart, J., Corbel, C., Jockers, R., Bach, S., and Couturier, C. (2008) The BRET technology and its application to screening assays. *Biotechnol J* 3, 311-324
25. Bhathena, S. J., Oie, H. K., Gazdar, A. F., Voyles, N. R., Wilkins, S. D., and Recant, L. (1982) Insulin, glucagon, and somatostatin receptors on cultured cells and clones from rat islet cell tumor. *Diabetes* 31, 521-531

26. Philippe, J., Chick, W. L., and Habener, J. F. (1987) Multipotential phenotypic expression of genes encoding peptide hormones in rat insulinoma cell lines. *J. Clin. Invest.* 79, 351-358
27. Korman, L. Y., Bhathena, S. J., Voyles, N. R., Oie, H. K., and Recant, L. (1985) Characteristics of the interaction of the glucagon receptor, cAMP, and insulin secretion in parent cells and clone 5F of a cultured rat insulinoma. *Diabetes* 34, 717-722
28. Gallwitz, B., Witt, M., Folsch, U. R., Creutzfeldt, W., and Schmidt, W. E. (1993) Binding specificity and signal transduction of receptors for glucagon-like peptide-1 (7-36)amide and gastric inhibitory polypeptide on RINm5F insulinoma cells. *J. Mol. Endocrinol.* 10, 259-268
29. Oakley, R. H., Laporte, S. A., Holt, J. A., Barak, L. S., and Caron, M. G. (1999) Association of beta-arrestin with G protein-coupled receptors during clathrin-mediated endocytosis dictates the profile of receptor resensitization. *J Biol. Chem.* 274, 32248-32257
30. Kerr, B. D., Flatt, A. J., Flatt, P. R., and Gault, V. A. (2011) Characterization and biological actions of N-terminal truncated forms of glucose-dependent insulinotropic polypeptide. *Biochem. Biophys. Res. Commun.* 404, 870-876
31. Unson, C. G., Andreu, D., Gurzenda, E. M., and Merrifield, R. B. (1987) Synthetic peptide antagonists of glucagon. *Proc. Natl. Acad Sci. U.S.A* 84, 4083-4087
32. Gefel, D., Hendrick, G. K., Mojsov, S., Habener, J., and Weir, G. C. (1990) Glucagon-like peptide-I analogs: effects on insulin secretion and adenosine 3',5'-monophosphate formation. *Endocrinology* 126, 2164-2168
33. Salahpour, A., Espinoza, S., Masri, B., Lam, V., Barak, L. S., and Gainetdinov, R. R. (2012) BRET biosensors to study GPCR biology, pharmacology, and signal transduction. *Front. Endocrinol.* (Lausanne) 3, 1-9
34. Overton, H. A., Babbs, A. J., Doel, S. M., Fyfe, M. C., Gardner, L. S., Griffin, G., Jackson, H. C., Procter, M. J., Rasamison, C. M., Tang-Christensen, M., Widdowson, P. S., Williams, G. M., and Reynet, C. (2006) Deorphanization of a G protein-coupled receptor for oleoylethanolamide and its use in the discovery of small-molecule hypophagic agents. *Cell Metab* 3, 167-175
35. Chu, Z. L., Jones, R. M., He, H., Carroll, C., Gutierrez, V., Lucman, A., Moloney, M., Gao, H., Mondala, H., Bagnol, D., Unett, D., Liang, Y., Demarest, K., Semple, G., Behan, D. P., and Leonard, J. (2007) A role for beta-cell-expressed G protein-coupled receptor 119 in glycemic control by enhancing glucose-dependent insulin release. *Endocrinology* 148, 2601-2609
36. Ning, Y., O'Neill, K., Lan, H., Pang, L., Shan, L. X., Hawes, B. E., and Hedrick, J. A. (2008) Endogenous and synthetic agonists of GPRI 19 differ in signalling pathways and their effects on insulin secretion in MIN6c4 insulinoma cells. *Br. J. Pharmacol.* 155, 1056-1065
37. Adelhorst, K., Hedegaard, B. B., Knudsen, L. B., and Kirk, O. (1994) Structure-activity studies of glucagon-like peptide-1. *J. Biol. Chem.* 269, 6275-6278
38. Robinson, R. M., Blakeney, E. W., Jr., and Mattice, W. L. (1982) Lipid-induced conformational changes in glucagon, secretin, and vasoactive intestinal peptide. *Biopolymers* 21, 1271-1228
39. Parthier, C., Reedtz-Runge, S., Rudolph, R., and Stubbs, M. T. (2009) Passing the baton in class B GPCRs: peptide hormone activation via helix induction?*Trends Biochem. Sci.* 34, 303-310
40. Trapp, S., and Richards, J. E. (2013) The gut hormone glucagon-like peptide-1 produced in brain: is this physiologically relevant?*Curr. Opin. Pharmacol.* 13, 964-969
41. Aviles-Olmos, I., Dickson, J., Kefalopoulou, Z., Djamshidian, A., Ell, P., Soderlund, T., Whitton, P., Wyse, R., Isaacs, T., Lees, A., Limousin, P., and Foltynie, T. (2013) Exenatide and the treatment of patients with Parkinson's disease. *J Clin. Invest.* 123, 2730-2736
42. Yang, Y., Zhang, J., Ma, D., Zhang, M., Hu, S., Shao, S., and Gong, C. X. (2013) Subcutaneous administration of liraglutide ameliorates Alzheimer-associated tau hyperphosphorylation in rats with type 2 diabetes. *J Alzheimers Dis.* 37, 637-648
43. Kleberg, K., Hassing, H. A., and Hansen, H. S. (2014) Classical endocannabinoid-like compounds and their regulation by nutrients. *Biofactors* 40 (4) 363-372
44. Hara, T., Kimura, I., Inoue, D., Ichimura, A., and Hirasawa, A. (2013) Free fatty acid receptors and their role in regulation of energy metabolism. *Rev. Physiol. Biochem. Pharmacol.* 164, 77-116
45. Hermanson, D. J., Hartley, N. D., Gamble-George, J., Brown, N., Shonesy, B. C., Kingsley, P. J., Colbran, R. J., Reese, J., Marnett, L. J., and Patel, S. (2013) Substrate-selective COX-2 inhibition decreases anxiety via endocannabinoid activation. *Nat. Neurosci.* 16, 1291-1298
46. Richardson, D., Ortori, C. A., Chapman, V., Kendall, D. A., and Barrett, D. A. (2007) Quantitative profiling of endocannabinoids and related compounds in rat brain using liquid chromatography-tandem electrospray ionization mass spectrometry. *Anal. Biochem.* 360, 216-226
47. Calanna, S., Christensen, M., Hoist, J. J., Laferrere, B., Gluud, L. L., Vilsboll, T., and Knop, F. K. (2013) Secretion of glucagon-like peptide-1 in patients with type 2 diabetes mellitus: systematic review and meta-analyses of clinical studies. *Diabetologia* 56, 965-972
48. Bagger, J. I., Knop, F. K., Lund, A., Vestergaard, H., Holst, J. J., and Vilsboll, T. (2011) Impaired regulation of the incretin effect in patients with type 2 diabetes. *J. Clin. Endocrinol. Metab.* 96, 737-745
49. Wiedenkeller, D. E., and Sharp, G. W. (1983) Effects of forskolin on insulin release and cyclic AMP content in rat pancreatic islets. *Endocrinology* 113, 2311-2313

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and to conditions. Thus, other embodiments are also within the claims.

What is claimed is:

1. A cell expressing a biosensor for detecting cyclic adenosine monophosphate (cAMP), where the biosensor comprises a protein complex that comprises an exchange protein activated by cAMP (Epac) polypeptide, a *Renilla* luciferase (RLuc), and a green fluorescent protein (GFP), wherein the Epac polypeptide comprises the amino acid sequence of SEQ ID NO:2.

2. The cell of claim 1, wherein the RLuc is RLuc8 which comprises the amino acid sequence set forth in SEQ ID NO: 4, or the GFP is GFP2 which comprises the amino acid sequence set forth in SEQ ID NO: 5.

3. The cell of claim 2, wherein the protein complex is a fusion protein, in which the N-terminus and C-terminus of the Epac polypeptide is fused to the RLuc and GFP, respectively.

4. The cell of claim 3, wherein the fusion protein comprises the amino acid sequence of SEQ ID NO: 3.

5. The cell of claim 4, wherein the cell is a mammalian cell.

6. The cell of claim 5, wherein the mammalian cell is an insulin-secreting cell.

7. A method for determining the level of intracellular cyclic adenosine monophosphate (cAMP), comprising:
   culturing a cell that expresses a biosensor, wherein the biosensor comprises a protein complex comprising an exchange protein activated by cAMP (Epac) polypeptide, a *Renilla* luciferase (RLuc), and a green fluorescent protein (GFP), wherein the Epac polypeptide comprises the amino acid sequence of SEQ ID NO:2;
   adding to the cultured cell a substrate of the RLuc;
   measuring a first luminescent signal at a wave length of around 370-450 nm and a second luminescent signal at a wave length of 500-530 nm; and
   determining the level of intracellular cAMP in the cell based on a ratio of the second luminescent signal to the first luminescent signal.

8. The method of claim 7, wherein the RLuc is RLuc8 which comprises the amino acid sequence set forth in SEQ ID NO: 4, or the GFP is GFP2 which comprises the amino acid sequence set forth in SEQ ID NO: 5.

9. The method of claim 8, wherein the cAMP biosensor is a fusion protein, in which the N-terminus and C-terminus of the Epac polypeptide are fused to the RLuc and GFP.

10. The method of claim 9, wherein the fusion protein comprises the amino acid sequence of SEQ ID NO:3.

11. The method of claim 10, wherein the cell is a mammalian cell.

12. The method of claim 11, wherein the mammalian cell is an insulin-secreting cell.

* * * * *

SEQUENCE LISTING

<160> NUMBER OF SEQ ID NOS: 14

<210> SEQ ID NO 1
<211> LENGTH: 881
<212> TYPE: PRT
<213> ORGANISM: Homo sapiens

<400> SEQUENCE: 1

Met Val Leu Arg Arg Met His Arg Pro Arg Ser Cys Ser Tyr Gln Leu
1               5                   10                  15

Leu Leu Glu His Gln Arg Pro Ser Cys Ile Gln Gly Leu Arg Trp Thr
            20                  25                  30

Pro Leu Thr Asn Ser Glu Glu Ser Leu Asp Phe Ser Glu Ser Leu Glu
        35                  40                  45

Gln Ala Ser Thr Glu Arg Val Leu Arg Ala Gly Arg Gln Leu His Arg
    50                  55                  60

His Leu Leu Ala Thr Cys Pro Asn Leu Ile Arg Asp Arg Lys Tyr His
65                  70                  75                  80

Leu Arg Leu Tyr Arg Gln Cys Cys Ser Gly Arg Glu Leu Val Asp Gly
                85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
        115                 120                 125

Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
            180                 185                 190

Leu Ile Phe Glu Glu Leu Leu His Ile Lys Ala Val Ala His Leu Ser
        195                 200                 205

Asn Ser Val Lys Arg Glu Leu Ala Ala Val Leu Leu Phe Glu Pro His
    210                 215                 220

Ser Lys Ala Gly Thr Val Leu Phe Ser Gln Gly Asp Lys Gly Thr Ser
225                 230                 235                 240

Trp Tyr Ile Ile Trp Lys Gly Ser Val Asn Val Val Thr His Gly Lys
                245                 250                 255

Gly Leu Val Thr Thr Leu His Glu Gly Asp Asp Phe Gly Gln Leu Ala
            260                 265                 270

Leu Val Asn Asp Ala Pro Arg Ala Ala Thr Ile Ile Leu Arg Glu Asp
        275                 280                 285

Asn Cys His Phe Leu Arg Val Asp Lys Gln Asp Phe Asn Arg Ile Ile
    290                 295                 300

Lys Asp Val Glu Ala Lys Thr Met Arg Leu Glu Glu His Gly Lys Val
305                 310                 315                 320

Val Leu Val Leu Glu Arg Ala Ser Gln Gly Ala Gly Pro Ser Arg Pro
                325                 330                 335

Pro Thr Pro Gly Arg Asn Arg Tyr Thr Val Met Ser Gly Thr Pro Glu
            340                 345                 350

Lys Ile Leu Glu Leu Leu Leu Glu Ala Met Gly Pro Asp Ser Ser Ala
        355                 360                 365

-continued

```
His Asp Pro Thr Glu Thr Phe Leu Ser Asp Phe Leu Leu Thr His Arg
    370                 375                 380

Val Phe Met Pro Ser Ala Gln Leu Cys Ala Ala Leu Leu His His Phe
385                 390                 395                 400

His Val Glu Pro Ala Gly Gly Ser Gln Glu Arg Ser Thr Tyr Val
                    405                 410                 415

Cys Asn Lys Arg Gln Gln Ile Leu Arg Leu Val Ser Gln Trp Val Ala
                420                 425                 430

Leu Tyr Gly Ser Met Leu His Thr Asp Pro Val Ala Thr Ser Phe Leu
            435                 440                 445

Gln Lys Leu Ser Asp Leu Val Gly Arg Asp Thr Arg Leu Ser Asn Leu
    450                 455                 460

Leu Arg Glu Gln Trp Pro Glu Arg Arg Cys His Arg Leu Glu Asn
465                 470                 475                 480

Gly Cys Gly Asn Ala Ser Pro Gln Met Lys Ala Arg Asn Leu Pro Val
                485                 490                 495

Trp Leu Pro Asn Gln Asp Glu Pro Leu Pro Gly Ser Ser Cys Ala Ile
                500                 505                 510

Gln Val Gly Asp Lys Val Pro Tyr Asp Ile Cys Arg Pro Asp His Ser
    515                 520                 525

Val Leu Thr Leu Gln Leu Pro Val Thr Ala Ser Val Arg Glu Val Met
    530                 535                 540

Ala Ala Leu Ala Gln Glu Asp Gly Trp Thr Lys Gly Gln Val Leu Val
545                 550                 555                 560

Lys Val Asn Ser Ala Gly Asp Ala Ile Gly Leu Gln Pro Asp Ala Arg
                565                 570                 575

Gly Val Ala Thr Ser Leu Gly Leu Asn Glu Arg Leu Phe Val Val Asn
                580                 585                 590

Pro Gln Glu Val His Glu Leu Ile Pro His Pro Asp Gln Leu Gly Pro
    595                 600                 605

Thr Val Gly Ser Ala Glu Gly Leu Asp Leu Val Ser Ala Lys Asp Leu
    610                 615                 620

Ala Gly Gln Leu Thr Asp His Asp Trp Ser Leu Phe Asn Ser Ile His
625                 630                 635                 640

Gln Val Glu Leu Ile His Tyr Val Leu Gly Pro Gln His Leu Arg Asp
                645                 650                 655

Val Thr Thr Ala Asn Leu Glu Arg Phe Met Arg Arg Phe Asn Glu Leu
                660                 665                 670

Gln Tyr Trp Val Ala Thr Glu Leu Cys Leu Cys Pro Val Pro Gly Pro
    675                 680                 685

Arg Ala Gln Leu Leu Arg Lys Phe Ile Lys Leu Ala Ala His Leu Lys
    690                 695                 700

Glu Gln Lys Asn Leu Asn Ser Phe Phe Ala Val Met Phe Gly Leu Ser
705                 710                 715                 720

Asn Ser Ala Ile Ser Arg Leu Ala His Thr Trp Glu Arg Leu Pro His
                725                 730                 735

Lys Val Arg Lys Leu Tyr Ser Ala Leu Glu Arg Leu Leu Asp Pro Ser
                740                 745                 750

Trp Asn His Arg Val Tyr Arg Leu Ala Leu Ala Lys Leu Ser Pro Pro
            755                 760                 765

Val Ile Pro Phe Met Pro Leu Leu Leu Lys Asp Met Thr Phe Ile His
    770                 775                 780

Glu Gly Asn His Thr Leu Val Glu Asn Leu Ile Asn Phe Glu Lys Met
```

```
                785                 790                 795                 800
Arg Met Met Ala Arg Ala Ala Arg Met Leu His His Cys Arg Ser His
                    805                 810                 815

Asn Pro Val Pro Leu Ser Pro Leu Arg Ser Arg Val Ser His Leu His
                    820                 825                 830

Glu Asp Ser Gln Val Ala Arg Ile Ser Thr Cys Ser Glu Gln Ser Leu
                    835                 840                 845

Ser Thr Arg Ser Pro Ala Ser Thr Trp Ala Tyr Val Gln Gln Leu Lys
                    850                 855                 860

Val Ile Asp Asn Gln Arg Glu Leu Ser Arg Leu Ser Arg Glu Leu Glu
865                 870                 875                 880

Pro

<210> SEQ ID NO 2
<211> LENGTH: 734
<212> TYPE: PRT
<213> ORGANISM: artificial sequence
<220> FEATURE:
<223> OTHER INFORMATION: Epac with mutations

<400> SEQUENCE: 2

Glu Pro Val Gly Thr His Glu Met Glu Glu Leu Ala Glu Ala Val
1               5                   10                  15

Ala Leu Leu Ser Gln Arg Gly Pro Asp Ala Leu Leu Thr Val Ala Leu
                    20                  25                  30

Arg Lys Pro Pro Gly Gln Arg Thr Asp Glu Glu Leu Asp Leu Ile Phe
                    35                  40                  45

Glu Glu Leu Leu His Ile Lys Ala Val Ala His Leu Ser Asn Ser Val
    50                  55                  60

Lys Arg Glu Leu Ala Ala Val Leu Leu Phe Glu Pro His Ser Lys Ala
65                  70                  75                  80

Gly Thr Val Leu Phe Ser Gln Gly Asp Lys Gly Thr Ser Trp Tyr Ile
                    85                  90                  95

Ile Trp Lys Gly Ser Val Asn Val Val Thr His Gly Lys Gly Leu Val
                    100                 105                 110

Thr Thr Leu His Glu Gly Asp Asp Phe Gly Gln Leu Ala Leu Val Asn
                    115                 120                 125

Asp Ala Pro Arg Ala Ala Thr Ile Ile Leu Arg Glu Asp Asn Cys His
    130                 135                 140

Phe Leu Arg Val Asp Lys Gln Asp Phe Asn Arg Ile Ile Lys Asp Val
145                 150                 155                 160

Glu Ala Lys Thr Met Arg Leu Glu Glu His Gly Lys Val Val Leu Val
                    165                 170                 175

Leu Glu Arg Ala Ser Gln Gly Ala Gly Pro Ser Arg Pro Pro Thr Pro
                    180                 185                 190

Gly Arg Asn Arg Tyr Thr Val Met Ser Gly Thr Pro Glu Lys Ile Leu
                    195                 200                 205

Glu Leu Leu Leu Glu Ala Met Gly Pro Asp Ser Ser Ala His Asp Pro
    210                 215                 220

Thr Glu Thr Phe Leu Ser Asp Phe Leu Leu Thr His Arg Val Phe Met
225                 230                 235                 240

Pro Ser Ala Gln Leu Cys Ala Ala Leu Leu His His Phe His Val Glu
                    245                 250                 255

Pro Ala Gly Gly Ser Glu Gln Glu Arg Ser Thr Tyr Val Cys Asn Lys
                    260                 265                 270
```

```
Arg Gln Gln Ile Leu Arg Leu Val Ser Gln Trp Val Ala Leu Tyr Gly
            275                 280                 285
Ser Met Leu His Thr Asp Pro Val Ala Thr Ser Phe Leu Gln Lys Leu
        290                 295                 300
Ser Asp Leu Val Gly Arg Asp Thr Arg Leu Ser Asn Leu Leu Arg Glu
305                 310                 315                 320
Gln Trp Pro Glu Arg Arg Cys His Arg Leu Glu Asn Gly Cys Gly
                325                 330                 335
Asn Ala Ser Pro Gln Met Lys Ala Arg Asn Leu Pro Val Trp Leu Pro
                340                 345                 350
Asn Gln Asp Glu Pro Leu Pro Gly Ser Ser Cys Ala Ile Gln Val Gly
            355                 360                 365
Asp Lys Val Pro Tyr Asp Ile Cys Arg Pro Asp His Ser Val Leu Thr
        370                 375                 380
Leu Gln Leu Pro Val Thr Ala Ser Val Arg Glu Val Met Ala Ala Leu
385                 390                 395                 400
Ala Gln Glu Asp Gly Trp Thr Lys Gly Gln Val Leu Val Lys Val Asn
                405                 410                 415
Ser Ala Gly Asp Ala Ile Gly Leu Gln Pro Asp Ala Arg Gly Val Ala
                420                 425                 430
Thr Ser Leu Gly Leu Asn Glu Arg Leu Phe Val Val Asn Pro Gln Glu
        435                 440                 445
Val His Glu Leu Ile Pro His Pro Asp Gln Leu Gly Pro Thr Val Gly
        450                 455                 460
Ser Ala Glu Gly Leu Asp Leu Val Ser Ala Lys Asp Leu Ala Gly Gln
465                 470                 475                 480
Leu Thr Asp His Asp Trp Ser Leu Phe Asn Ser Ile His Gln Val Glu
                485                 490                 495
Leu Ile His Tyr Val Leu Gly Pro Gln His Leu Arg Asp Val Thr Thr
                500                 505                 510
Ala Asn Leu Glu Arg Phe Met Arg Arg Phe Asn Glu Leu Gln Tyr Trp
        515                 520                 525
Val Ala Thr Glu Leu Cys Leu Cys Pro Val Pro Gly Pro Arg Ala Gln
        530                 535                 540
Leu Leu Arg Lys Phe Ile Lys Leu Ala Ala His Leu Lys Glu Gln Lys
545                 550                 555                 560
Asn Leu Asn Ser Phe Phe Ala Val Met Phe Gly Leu Ser Asn Ser Ala
                565                 570                 575
Ile Ser Arg Leu Ala His Thr Trp Glu Arg Leu Pro His Lys Val Arg
                580                 585                 590
Lys Leu Tyr Ser Ala Leu Glu Arg Leu Leu Asp Pro Ser Trp Asn His
        595                 600                 605
Arg Val Tyr Arg Leu Ala Leu Ala Lys Leu Ser Pro Pro Val Ile Pro
        610                 615                 620
Phe Met Pro Leu Leu Leu Lys Asp Met Ala Ala Ile His Glu Gly Asn
625                 630                 635                 640
His Thr Leu Val Glu Asn Leu Ile Asn Phe Glu Lys Met Arg Met Met
                645                 650                 655
Ala Arg Ala Ala Arg Met Leu His His Cys Arg Ser His Asn Pro Val
                660                 665                 670
Pro Leu Ser Pro Leu Arg Ser Arg Val Ser His Leu His Glu Asp Ser
        675                 680                 685
```

-continued

```
Gln Val Ala Arg Ile Ser Thr Cys Ser Glu Gln Ser Leu Ser Thr Arg
    690                 695                 700
Ser Pro Ala Ser Thr Trp Ala Tyr Val Gln Gln Leu Lys Val Ile Asp
705                 710                 715                 720
Asn Gln Arg Glu Leu Ser Arg Leu Ser Arg Glu Leu Glu Pro
                725                 730

<210> SEQ ID NO 3
<211> LENGTH: 1289
<212> TYPE: PRT
<213> ORGANISM: Artificial Sequence
<220> FEATURE:
<223> OTHER INFORMATION: Fusion protein of Epac polypeptide with RLuc
      and GFP.

<400> SEQUENCE: 3

Met Ala Ser Lys Val Tyr Asp Pro Glu Gln Arg Lys Arg Met Ile Thr
1               5                  10                  15
Gly Pro Gln Trp Trp Ala Arg Cys Lys Gln Met Asn Val Leu Asp Ser
                20                  25                  30
Phe Ile Asn Tyr Tyr Asp Ser Glu Lys His Ala Glu Asn Ala Val Ile
            35                  40                  45
Phe Leu His Gly Asn Ala Thr Ser Ser Tyr Leu Trp Arg His Val Val
        50                  55                  60
Pro His Ile Glu Pro Val Ala Arg Cys Ile Ile Pro Asp Leu Ile Gly
65                  70                  75                  80
Met Gly Lys Ser Gly Lys Ser Gly Asn Gly Ser Tyr Arg Leu Leu Asp
                85                  90                  95
His Tyr Lys Tyr Leu Thr Ala Trp Phe Glu Leu Leu Asn Leu Pro Lys
            100                 105                 110
Lys Ile Ile Phe Val Gly His Asp Trp Gly Ala Ala Leu Ala Phe His
        115                 120                 125
Tyr Ala Tyr Glu His Gln Asp Arg Ile Lys Ala Ile Val His Met Glu
    130                 135                 140
Ser Val Val Asp Val Ile Glu Ser Trp Asp Glu Trp Pro Asp Ile Glu
145                 150                 155                 160
Glu Asp Ile Ala Leu Ile Lys Ser Glu Glu Gly Glu Lys Met Val Leu
                165                 170                 175
Glu Asn Asn Phe Phe Val Glu Thr Val Leu Pro Ser Lys Ile Met Arg
            180                 185                 190
Lys Leu Glu Pro Glu Glu Phe Ala Ala Tyr Leu Glu Pro Phe Lys Glu
        195                 200                 205
Lys Gly Glu Val Arg Arg Pro Thr Leu Ser Trp Pro Arg Glu Ile Pro
    210                 215                 220
Leu Val Lys Gly Gly Lys Pro Asp Val Val Gln Ile Val Arg Asn Tyr
225                 230                 235                 240
Asn Ala Tyr Leu Arg Ala Ser Asp Asp Leu Pro Lys Leu Phe Ile Glu
                245                 250                 255
Ser Asp Pro Gly Phe Phe Ser Asn Ala Ile Val Glu Gly Ala Lys Lys
            260                 265                 270
Phe Pro Asn Thr Glu Phe Val Lys Val Lys Gly Leu His Phe Leu Gln
        275                 280                 285
Glu Asp Ala Pro Asp Glu Met Gly Lys Tyr Ile Lys Ser Phe Val Glu
    290                 295                 300
Arg Val Leu Lys Asn Glu Gln Leu Gly Leu Glu Pro Val Gly Thr His
305                 310                 315                 320
```

```
Glu Met Glu Glu Glu Leu Ala Glu Ala Val Ala Leu Leu Ser Gln Arg
            325                 330                 335
Gly Pro Asp Ala Leu Leu Thr Val Ala Leu Arg Lys Pro Pro Gly Gln
            340                 345                 350
Arg Thr Asp Glu Glu Leu Asp Leu Ile Phe Glu Glu Leu Leu His Ile
            355                 360                 365
Lys Ala Val Ala His Leu Ser Asn Ser Val Lys Arg Glu Leu Ala Ala
            370                 375                 380
Val Leu Leu Phe Glu Pro His Ser Lys Ala Gly Thr Val Leu Phe Ser
385                 390                 395                 400
Gln Gly Asp Lys Gly Thr Ser Trp Tyr Ile Ile Trp Lys Gly Ser Val
            405                 410                 415
Asn Val Val Thr His Gly Lys Gly Leu Val Thr Thr Leu His Glu Gly
            420                 425                 430
Asp Asp Phe Gly Gln Leu Ala Leu Val Asn Asp Ala Pro Arg Ala Ala
            435                 440                 445
Thr Ile Ile Leu Arg Glu Asp Asn Cys His Phe Leu Arg Val Asp Lys
            450                 455                 460
Gln Asp Phe Asn Arg Ile Ile Lys Asp Val Glu Ala Lys Thr Met Arg
465                 470                 475                 480
Leu Glu Glu His Gly Lys Val Val Leu Val Leu Glu Arg Ala Ser Gln
            485                 490                 495
Gly Ala Gly Pro Ser Arg Pro Pro Thr Pro Gly Arg Asn Arg Tyr Thr
            500                 505                 510
Val Met Ser Gly Thr Pro Glu Lys Ile Leu Glu Leu Leu Leu Glu Ala
            515                 520                 525
Met Gly Pro Asp Ser Ser Ala His Asp Pro Thr Glu Thr Phe Leu Ser
            530                 535                 540
Asp Phe Leu Leu Thr His Arg Val Phe Met Pro Ser Ala Gln Leu Cys
545                 550                 555                 560
Ala Ala Leu Leu His His Phe His Val Glu Pro Ala Gly Gly Ser Glu
            565                 570                 575
Gln Glu Arg Ser Thr Tyr Val Cys Asn Lys Arg Gln Gln Ile Leu Arg
            580                 585                 590
Leu Val Ser Gln Trp Val Ala Leu Tyr Gly Ser Met Leu His Thr Asp
            595                 600                 605
Pro Val Ala Thr Ser Phe Leu Gln Lys Leu Ser Asp Leu Val Gly Arg
            610                 615                 620
Asp Thr Arg Leu Ser Asn Leu Leu Arg Glu Gln Trp Pro Glu Arg Arg
625                 630                 635                 640
Arg Cys His Arg Leu Glu Asn Gly Cys Gly Asn Ala Ser Pro Gln Met
            645                 650                 655
Lys Ala Arg Asn Leu Pro Val Trp Leu Pro Asn Gln Asp Glu Pro Leu
            660                 665                 670
Pro Gly Ser Ser Cys Ala Ile Gln Val Gly Asp Lys Val Pro Tyr Asp
            675                 680                 685
Ile Cys Arg Pro Asp His Ser Val Leu Thr Leu Gln Leu Pro Val Thr
            690                 695                 700
Ala Ser Val Arg Glu Val Met Ala Ala Leu Ala Gln Glu Asp Gly Trp
705                 710                 715                 720
Thr Lys Gly Gln Val Leu Val Lys Val Asn Ser Ala Gly Asp Ala Ile
            725                 730                 735
```

```
Gly Leu Gln Pro Asp Ala Arg Gly Val Ala Thr Ser Leu Gly Leu Asn
            740                 745                 750

Glu Arg Leu Phe Val Val Asn Pro Gln Glu Val His Glu Leu Ile Pro
            755                 760                 765

His Pro Asp Gln Leu Gly Pro Thr Val Gly Ser Ala Glu Gly Leu Asp
        770                 775                 780

Leu Val Ser Ala Lys Asp Leu Ala Gly Gln Leu Thr Asp His Asp Trp
785                 790                 795                 800

Ser Leu Phe Asn Ser Ile His Gln Val Glu Leu Ile His Tyr Val Leu
                805                 810                 815

Gly Pro Gln His Leu Arg Asp Val Thr Thr Ala Asn Leu Glu Arg Phe
            820                 825                 830

Met Arg Arg Phe Asn Glu Leu Gln Tyr Trp Val Ala Thr Glu Leu Cys
            835                 840                 845

Leu Cys Pro Val Pro Gly Pro Arg Ala Gln Leu Leu Arg Lys Phe Ile
        850                 855                 860

Lys Leu Ala Ala His Leu Lys Glu Gln Lys Asn Leu Asn Ser Phe Phe
865                 870                 875                 880

Ala Val Met Phe Gly Leu Ser Asn Ser Ala Ile Ser Arg Leu Ala His
                885                 890                 895

Thr Trp Glu Arg Leu Pro His Lys Val Arg Lys Leu Tyr Ser Ala Leu
            900                 905                 910

Glu Arg Leu Leu Asp Pro Ser Trp Asn His Arg Val Tyr Arg Leu Ala
            915                 920                 925

Leu Ala Lys Leu Ser Pro Pro Val Ile Pro Phe Met Pro Leu Leu Leu
        930                 935                 940

Lys Asp Met Ala Ala Ile His Glu Gly Asn His Thr Leu Val Glu Asn
945                 950                 955                 960

Leu Ile Asn Phe Glu Lys Met Arg Met Met Ala Arg Ala Ala Arg Met
                965                 970                 975

Leu His His Cys Arg Ser His Asn Pro Val Pro Leu Ser Pro Leu Arg
            980                 985                 990

Ser Arg Val Ser His Leu His Glu Asp Ser Gln Val Ala Arg Ile Ser
            995                 1000                1005

Thr Cys Ser Glu Gln Ser Leu Ser Thr Arg Ser Pro Ala Ser Thr
        1010                1015                1020

Trp Ala Tyr Val Gln Gln Leu Lys Val Ile Asp Asn Gln Arg Glu
        1025                1030                1035

Leu Ser Arg Leu Ser Arg Glu Leu Glu Pro Ala Thr Met Val Ser
        1040                1045                1050

Lys Gly Glu Glu Leu Phe Thr Gly Val Val Pro Ile Leu Val Glu
        1055                1060                1065

Leu Asp Gly Asp Val Asn Gly His Lys Phe Ser Val Ser Gly Glu
        1070                1075                1080

Gly Glu Gly Asp Ala Thr Tyr Gly Lys Leu Thr Leu Lys Phe Ile
        1085                1090                1095

Cys Thr Thr Gly Lys Leu Pro Val Pro Trp Pro Thr Leu Val Thr
        1100                1105                1110

Thr Leu Ser Tyr Gly Val Gln Cys Phe Ser Arg Tyr Pro Asp His
        1115                1120                1125

Met Lys Gln His Asp Phe Phe Lys Ser Ala Met Pro Glu Gly Tyr
        1130                1135                1140

Val Gln Glu Arg Thr Ile Phe Phe Lys Asp Asp Gly Asn Tyr Lys
```

```
            1145                1150                1155

Thr Arg Ala Glu Val Lys Phe Glu Gly Asp Thr Leu Val Asn Arg
        1160                1165                1170

Ile Glu Leu Lys Gly Ile Asp Phe Lys Glu Asp Gly Asn Ile Leu
    1175                1180                1185

Gly His Lys Leu Glu Tyr Asn Tyr Asn Ser His Asn Val Tyr Ile
        1190                1195                1200

Met Ala Asp Lys Gln Lys Asn Gly Ile Lys Val Asn Phe Lys Ile
    1205                1210                1215

Arg His Asn Ile Glu Asp Gly Ser Val Gln Leu Ala Asp His Tyr
    1220                1225                1230

Gln Gln Asn Thr Pro Ile Gly Asp Gly Pro Val Leu Leu Pro Asp
    1235                1240                1245

Asn His Tyr Leu Ser Thr Gln Ser Ala Leu Ser Lys Asp Pro Asn
    1250                1255                1260

Glu Lys Arg Asp His Met Val Leu Leu Glu Phe Val Thr Ala Ala
    1265                1270                1275

Gly Ile Thr Leu Gly Met Asp Glu Leu Tyr Lys
    1280                1285

<210> SEQ ID NO 4
<211> LENGTH: 311
<212> TYPE: PRT
<213> ORGANISM: Renilla reniformis

<400> SEQUENCE: 4

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220
```

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Leu Phe Ile Glu
            245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Leu Gln
            275                 280                 285

Glu Asp Ala Pro Asp Glu Met Gly Lys Tyr Ile Lys Ser Phe Val Glu
            290                 295                 300

Arg Val Leu Lys Asn Glu Gln
305                 310

<210> SEQ ID NO 5
<211> LENGTH: 239
<212> TYPE: PRT
<213> ORGANISM: Aequorea victoria

<400> SEQUENCE: 5

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 6
<211> LENGTH: 36
<212> TYPE: PRT
<213> ORGANISM: Artificial Sequence
<220> FEATURE:
<223> OTHER INFORMATION: His-tagged GLP-1 (7-36)

```
<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His His
            20                  25                  30

His His His His
        35

<210> SEQ ID NO 7
<211> LENGTH: 734
<212> TYPE: PRT
<213> ORGANISM: Artificial Sequence
<220> FEATURE:
<223> OTHER INFORMATION: A truncated mutant of Epac polypeptide lacking
      N-terminal 1-147 aa

<400> SEQUENCE: 7

Glu Pro Val Gly Thr His Glu Met Glu Glu Leu Ala Glu Ala Val
1               5                   10                  15

Ala Leu Leu Ser Gln Arg Gly Pro Asp Ala Leu Leu Thr Val Ala Leu
            20                  25                  30

Arg Lys Pro Pro Gly Gln Arg Thr Asp Glu Glu Leu Asp Leu Ile Phe
        35                  40                  45

Glu Glu Leu Leu His Ile Lys Ala Val Ala His Leu Ser Asn Ser Val
50                  55                  60

Lys Arg Glu Leu Ala Ala Val Leu Leu Phe Glu Pro His Ser Lys Ala
65                  70                  75                  80

Gly Thr Val Leu Phe Ser Gln Gly Asp Lys Gly Thr Ser Trp Tyr Ile
                85                  90                  95

Ile Trp Lys Gly Ser Val Asn Val Val Thr His Gly Lys Gly Leu Val
            100                 105                 110

Thr Thr Leu His Glu Gly Asp Asp Phe Gly Gln Leu Ala Leu Val Asn
        115                 120                 125

Asp Ala Pro Arg Ala Ala Thr Ile Ile Leu Arg Glu Asp Asn Cys His
130                 135                 140

Phe Leu Arg Val Asp Lys Gln Asp Phe Asn Arg Ile Ile Lys Asp Val
145                 150                 155                 160

Glu Ala Lys Thr Met Arg Leu Glu Glu His Gly Lys Val Val Leu Val
                165                 170                 175

Leu Glu Arg Ala Ser Gln Gly Ala Gly Pro Ser Arg Pro Pro Thr Pro
            180                 185                 190

Gly Arg Asn Arg Tyr Thr Val Met Ser Gly Thr Pro Glu Lys Ile Leu
        195                 200                 205

Glu Leu Leu Leu Glu Ala Met Gly Pro Asp Ser Ala His Asp Pro
210                 215                 220

Thr Glu Thr Phe Leu Ser Asp Phe Leu Leu Thr His Arg Val Phe Met
225                 230                 235                 240

Pro Ser Ala Gln Leu Cys Ala Ala Leu Leu His His Phe His Val Glu
                245                 250                 255

Pro Ala Gly Gly Ser Glu Gln Glu Arg Ser Thr Tyr Val Cys Asn Lys
            260                 265                 270

Arg Gln Gln Ile Leu Arg Leu Val Ser Gln Trp Val Ala Leu Tyr Gly
        275                 280                 285

Ser Met Leu His Thr Asp Pro Val Ala Thr Ser Phe Leu Gln Lys Leu
290                 295                 300
```

```
Ser Asp Leu Val Gly Arg Asp Thr Arg Leu Ser Asn Leu Leu Arg Glu
305                 310                 315                 320

Gln Trp Pro Glu Arg Arg Cys His Arg Leu Glu Asn Gly Cys Gly
            325                 330                 335

Asn Ala Ser Pro Gln Met Lys Ala Arg Asn Leu Pro Val Trp Leu Pro
            340                 345                 350

Asn Gln Asp Glu Pro Leu Pro Gly Ser Ser Cys Ala Ile Gln Val Gly
            355                 360                 365

Asp Lys Val Pro Tyr Asp Ile Cys Arg Pro Asp His Ser Val Leu Thr
370                 375                 380

Leu Gln Leu Pro Val Thr Ala Ser Val Arg Glu Val Met Ala Ala Leu
385                 390                 395                 400

Ala Gln Glu Asp Gly Trp Thr Lys Gly Gln Val Leu Val Lys Val Asn
            405                 410                 415

Ser Ala Gly Asp Ala Ile Gly Leu Gln Pro Asp Ala Arg Gly Val Ala
            420                 425                 430

Thr Ser Leu Gly Leu Asn Glu Arg Leu Phe Val Val Asn Pro Gln Glu
            435                 440                 445

Val His Glu Leu Ile Pro His Pro Asp Gln Leu Gly Pro Thr Val Gly
450                 455                 460

Ser Ala Glu Gly Leu Asp Leu Val Ser Ala Lys Asp Leu Ala Gly Gln
465                 470                 475                 480

Leu Thr Asp His Asp Trp Ser Leu Phe Asn Ser Ile His Gln Val Glu
            485                 490                 495

Leu Ile His Tyr Val Leu Gly Pro Gln His Leu Arg Asp Val Thr Thr
            500                 505                 510

Ala Asn Leu Glu Arg Phe Met Arg Arg Phe Asn Glu Leu Gln Tyr Trp
            515                 520                 525

Val Ala Thr Glu Leu Cys Leu Cys Pro Val Pro Gly Pro Arg Ala Gln
530                 535                 540

Leu Leu Arg Lys Phe Ile Lys Leu Ala Ala His Leu Lys Glu Gln Lys
545                 550                 555                 560

Asn Leu Asn Ser Phe Phe Ala Val Met Phe Gly Leu Ser Asn Ser Ala
            565                 570                 575

Ile Ser Arg Leu Ala His Thr Trp Glu Arg Leu Pro His Lys Val Arg
            580                 585                 590

Lys Leu Tyr Ser Ala Leu Glu Arg Leu Leu Asp Pro Ser Trp Asn His
            595                 600                 605

Arg Val Tyr Arg Leu Ala Leu Ala Lys Leu Ser Pro Pro Val Ile Pro
610                 615                 620

Phe Met Pro Leu Leu Leu Lys Asp Met Thr Phe Ile His Glu Gly Asn
625                 630                 635                 640

His Thr Leu Val Glu Asn Leu Ile Asn Phe Glu Lys Met Arg Met Met
            645                 650                 655

Ala Arg Ala Ala Arg Met Leu His His Cys Arg Ser His Asn Pro Val
            660                 665                 670

Pro Leu Ser Pro Leu Arg Ser Arg Val Ser His Leu His Glu Asp Ser
            675                 680                 685

Gln Val Ala Arg Ile Ser Thr Cys Ser Glu Gln Ser Leu Ser Thr Arg
            690                 695                 700

Ser Pro Ala Ser Thr Trp Ala Tyr Val Gln Gln Leu Lys Val Ile Asp
705                 710                 715                 720

Asn Gln Arg Glu Leu Ser Arg Leu Ser Arg Glu Leu Glu Pro
```

<210> SEQ ID NO 8
<211> LENGTH: 283
<212> TYPE: PRT
<213> ORGANISM: Artificial Sequence
<220> FEATURE:
<223> OTHER INFORMATION: Epac 1 (148-430aa)

<400> SEQUENCE: 8

```
Glu Pro Val Gly Thr His Glu Met Glu Glu Leu Ala Glu Ala Val
1               5                   10                  15

Ala Leu Leu Ser Gln Arg Gly Pro Asp Ala Leu Leu Thr Val Ala Leu
                20                  25                  30

Arg Lys Pro Pro Gly Gln Arg Thr Asp Glu Glu Leu Asp Leu Ile Phe
            35                  40                  45

Glu Glu Leu Leu His Ile Lys Ala Val Ala His Leu Ser Asn Ser Val
        50                  55                  60

Lys Arg Glu Leu Ala Ala Val Leu Leu Phe Glu Pro His Ser Lys Ala
65                  70                  75                  80

Gly Thr Val Leu Phe Ser Gln Gly Asp Lys Gly Thr Ser Trp Tyr Ile
                85                  90                  95

Ile Trp Lys Gly Ser Val Asn Val Val Thr His Gly Lys Gly Leu Val
            100                 105                 110

Thr Thr Leu His Glu Gly Asp Asp Phe Gly Gln Leu Ala Leu Val Asn
        115                 120                 125

Asp Ala Pro Arg Ala Ala Thr Ile Ile Leu Arg Glu Asp Asn Cys His
130                 135                 140

Phe Leu Arg Val Asp Lys Gln Asp Phe Asn Arg Ile Ile Lys Asp Val
145                 150                 155                 160

Glu Ala Lys Thr Met Arg Leu Glu Glu His Gly Lys Val Val Leu Val
                165                 170                 175

Leu Glu Arg Ala Ser Gln Gly Ala Gly Pro Ser Arg Pro Pro Thr Pro
            180                 185                 190

Gly Arg Asn Arg Tyr Thr Val Met Ser Gly Thr Pro Glu Lys Ile Leu
        195                 200                 205

Glu Leu Leu Leu Glu Ala Met Gly Pro Asp Ser Ser Ala His Asp Pro
210                 215                 220

Thr Glu Thr Phe Leu Ser Asp Phe Leu Leu Thr His Arg Val Phe Met
225                 230                 235                 240

Pro Ser Ala Gln Leu Cys Ala Ala Leu Leu His His Phe His Val Glu
                245                 250                 255

Pro Ala Gly Gly Ser Glu Gln Glu Arg Ser Thr Tyr Val Cys Asn Lys
            260                 265                 270

Arg Gln Gln Ile Leu Arg Leu Val Ser Gln Trp
        275                 280
```

<210> SEQ ID NO 9
<211> LENGTH: 30
<212> TYPE: PRT
<213> ORGANISM: artificial sequence
<220> FEATURE:
<223> OTHER INFORMATION: GLP-1 (7-36 aa)

<400> SEQUENCE: 9

```
His Ala Glu Gly Thr Phe Thr Ser Asp Val Ser Ser Tyr Leu Glu Gly
1               5                   10                  15
```

Gln Ala Ala Lys Glu Phe Ile Ala Trp Leu Val Lys Gly Arg
            20                  25                  30

<210> SEQ ID NO 10
<211> LENGTH: 28
<212> TYPE: PRT
<213> ORGANISM: Artificial Sequence
<220> FEATURE:
<223> OTHER INFORMATION: GLP 7-34

<400> SEQUENCE: 10

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

<210> SEQ ID NO 11
<211> LENGTH: 20
<212> TYPE: PRT
<213> ORGANISM: Artificial Sequence
<220> FEATURE:
<223> OTHER INFORMATION: GLP7-26

<400> SEQUENCE: 11

His Ala Glu Gly Thr Phe Thr Ser Asp Val Ser Ser Tyr Leu Glu Gly
1               5                   10                  15

Gln Ala Ala Lys
            20

<210> SEQ ID NO 12
<211> LENGTH: 153
<212> TYPE: PRT
<213> ORGANISM: Homo sapiens

<400> SEQUENCE: 12

Met Val Ala Thr Lys Thr Phe Ala Leu Leu Leu Ser Leu Phe Leu
1               5                   10                  15

Ala Val Gly Leu Gly Glu Lys Lys Glu Gly His Phe Ser Ala Leu Pro
                20                  25                  30

Ser Leu Pro Val Gly Ser His Ala Lys Val Ser Ser Pro Gln Pro Arg
            35                  40                  45

Gly Pro Arg Tyr Ala Glu Gly Thr Phe Ile Ser Asp Tyr Ser Ile Ala
        50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
        115                 120                 125

Leu Arg Asp Leu Leu Ile Gln Glu Leu Leu Ala Cys Leu Leu Asp Gln
130                 135                 140

Thr Asn Leu Cys Arg Leu Arg Ser Arg
145                 150

<210> SEQ ID NO 13
<211> LENGTH: 42
<212> TYPE: PRT
<213> ORGANISM: Homo sapiens

```
<400> SEQUENCE: 13

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 14
<211> LENGTH: 35
<212> TYPE: PRT
<213> ORGANISM: Artificial Sequence
<220> FEATURE:
<223> OTHER INFORMATION: GIP 8-42

<400> SEQUENCE: 14

Ser Asp Tyr Ser Ile Ala Met Asp Lys Ile His Gln Gln Asp Phe Val
1               5                   10                  15

Asn Trp Leu Leu Ala Gln Lys Gly Lys Lys Asn Asp Trp Lys His Asn
            20                  25                  30

Ile Thr Gln
        35
```